(12) United States Patent
Costella et al.

(10) Patent No.: US 12,383,695 B2
(45) Date of Patent: Aug. 12, 2025

(54) RESPIRATORY CARE SYSTEM WITH ELECTRONIC INDICATOR

(71) Applicant: Trudell Medical international Inc., London (CA)

(72) Inventors: Stephen Costella, London (CA); Alanna Kirchner, London (CA); Bart Nowak, London (CA); Neritan Alizoti, London (CA); Adam Meyer, London (CA); Greg Romanczuk, London (CA); Ronak Sakaria, London (CA)

(73) Assignee: Trudell Medical International Inc., London (CA)

( * ) Notice: Subject to any disclaimer, the term of this patent is extended or adjusted under 35 U.S.C. 154(b) by 1225 days.

(21) Appl. No.: 17/147,240

(22) Filed: Jan. 12, 2021

(65) Prior Publication Data

US 2021/0236764 A1 Aug. 5, 2021

Related U.S. Application Data

(63) Continuation of application No. 15/467,450, filed on Mar. 23, 2017, now Pat. No. 10,894,142.
(Continued)

(51) Int. Cl.
*A61M 16/20* (2006.01)
*A61M 11/06* (2006.01)
(Continued)

(52) U.S. Cl.
CPC .......... *A61M 16/202* (2014.02); *A61M 11/06* (2013.01); *A61M 15/0015* (2014.02);
(Continued)

(58) Field of Classification Search
CPC . A61B 18/1492; A61B 18/04; A61B 18/1477; A61B 17/3403; A61B 17/3478;
(Continued)

(56) References Cited

U.S. PATENT DOCUMENTS 3,624,568 A * 11/1971 Olsen .................. H01H 51/285
335/53
3,777,727 A * 12/1973 Kirchner ................ F02M 69/20
261/50.2
(Continued)

FOREIGN PATENT DOCUMENTS

CA 2607458 A1 11/2011
DE 102010024912 B4 2/2013
(Continued)

OTHER PUBLICATIONS

International Search Report in International Application No. PCT/IB2017/051695 dated Mar. 23, 2017, 8 pages.
(Continued)

*Primary Examiner* — Nathan R Price
*Assistant Examiner* — Mark A Igel
(74) *Attorney, Agent, or Firm* — Crowell & Moring LLP

(57) ABSTRACT

A respiratory care system includes a user interface. A flow indicator is moveable in response to inhalation and/or exhalation, or both, by a user through the user interface. An electronic indicator is operable in response to an electronic signal transmitted in response to the movement of the flow indicator. Methods of use and assembly are also provided.

17 Claims, 36 Drawing Sheets

Related U.S. Application Data

(60) Provisional application No. 62/465,479, filed on Mar. 1, 2017, provisional application No. 62/337,626, filed on May 17, 2016, provisional application No. 62/312,830, filed on Mar. 24, 2016.

(51) Int. Cl.
*A61M 15/00* (2006.01)
*A61M 16/00* (2006.01)
*A61M 16/06* (2006.01)
*A61M 16/16* (2006.01)

(52) U.S. Cl.
CPC ...... *A61M 15/008* (2014.02); *A61M 15/0086* (2013.01); *A61M 15/009* (2013.01); *A61M 16/06* (2013.01); *A61M 16/16* (2013.01); *A61M 15/0021* (2014.02); *A61M 2016/0024* (2013.01); *A61M 2016/0036* (2013.01); *A61M 2202/064* (2013.01); *A61M 2205/3306* (2013.01); *A61M 2205/3317* (2013.01); *A61M 2205/332* (2013.01); *A61M 2205/3331* (2013.01); *A61M 2205/3375* (2013.01); *A61M 2205/3561* (2013.01); *A61M 2205/3592* (2013.01); *A61M 2205/505* (2013.01); *A61M 2205/584* (2013.01); *A61M 2205/8206* (2013.01); *A61M 2206/14* (2013.01)

(58) Field of Classification Search
CPC ... A61B 90/39; A61B 2090/3966; A61B 5/24; A61B 5/0205; A61B 2017/22071; A61B 2018/0267; A61B 2018/00285; A61B 2018/0351; A61B 2018/00434; A61B 2018/00505; A61B 2018/547; A61B 2018/00577; A61B 2018/046; A61B 2018/048; A61B 2018/1425; A61B 2018/1475; A61M 25/0084; A61M 25/0662; A61M 5/158; A61M 2025/0004; A61M 2025/0087; A61M 2025/0186; A61M 2205/02; A61M 2205/32
See application file for complete search history.

(56) References Cited

U.S. PATENT DOCUMENTS

| | | | | |
|---|---|---|---|---|
| 3,921,637 A * | 11/1975 | Bennie | ......... | A61M 15/00 128/203.15 |
| 4,206,644 A * | 6/1980 | Platt | ......... | G01F 1/28 250/231.19 |
| 4,481,514 A * | 11/1984 | Beukers | ......... | G01W 1/08 340/870.1 |
| 4,500,866 A * | 2/1985 | Romann | ......... | F02D 41/182 338/185 |
| 4,662,564 A * | 5/1987 | Okuda | ......... | F02M 65/005 73/114.49 |
| 4,984,158 A * | 1/1991 | Hillsman | ......... | A61M 15/009 600/536 |
| 5,012,803 A * | 5/1991 | Foley | ......... | A61M 15/0086 128/203.29 |
| 5,012,804 A * | 5/1991 | Foley | ......... | A61M 15/009 128/203.29 |
| 5,042,467 A * | 8/1991 | Foley | ......... | A61M 15/0086 128/200.14 |
| 5,284,133 A | 2/1994 | Burns et al. | | |
| 5,331,953 A | 7/1994 | Andersson et al. | | |
| 5,333,106 A | 7/1994 | Lanpher et al. | | |
| 5,363,842 A * | 11/1994 | Mishelevich | ......... | A61M 15/008 128/200.14 |
| 5,431,154 A | 7/1995 | Seigel et al. | | |
| 5,477,849 A | 12/1995 | Fry | | |
| 5,505,192 A | 4/1996 | Samiotes et al. | | |
| 5,505,195 A * | 4/1996 | Wolf | ......... | A61M 15/0045 128/203.14 |
| 5,605,251 A * | 2/1997 | Retti | ......... | B05C 5/02 222/325 |
| 5,655,523 A * | 8/1997 | Hodson | ......... | A61M 15/0025 128/203.15 |
| 5,758,638 A | 6/1998 | Kreamer | | |
| 5,794,612 A | 8/1998 | Wachter et al. | | |
| 5,809,997 A | 9/1998 | Wolf | | |
| 5,819,726 A | 10/1998 | Rubsamen et al. | | |
| 5,848,588 A * | 12/1998 | Foley | ......... | A61M 15/0086 128/200.22 |
| 5,855,564 A * | 1/1999 | Ruskewicz | ......... | A61M 11/001 128/200.14 |
| 5,865,172 A | 2/1999 | Butler et al. | | |
| 5,937,852 A | 8/1999 | Butler et al. | | |
| 6,073,628 A | 6/2000 | Butler et al. | | |
| 6,125,844 A * | 10/2000 | Samiotes | ......... | A61M 15/0065 128/200.23 |
| 6,138,669 A | 10/2000 | Rocci, Jr. et al. | | |
| 6,148,815 A | 11/2000 | Wolf | | |
| 6,192,876 B1 | 2/2001 | Denyer et al. | | |
| 6,202,642 B1 | 3/2001 | McKinnon et al. | | |
| 6,234,167 B1 | 5/2001 | Cox et al. | | |
| 6,358,058 B1 | 3/2002 | Strupat et al. | | |
| 6,427,690 B1 * | 8/2002 | McCombs | ......... | A61M 16/022 128/205.24 |
| 6,450,163 B1 * | 9/2002 | Blacker | ......... | A61M 16/0666 128/200.14 |
| 6,578,571 B1 | 6/2003 | Watt | | |
| 6,651,651 B1 | 11/2003 | Bonney et al. | | |
| 6,684,879 B1 * | 2/2004 | Coffee | ......... | A61M 15/008 128/200.14 |
| 6,823,862 B2 | 11/2004 | McNaughton | | |
| 6,839,604 B2 | 1/2005 | Godfrey et al. | | |
| 6,880,722 B2 | 4/2005 | Anderson et al. | | |
| 6,904,907 B2 | 6/2005 | Speldrich et al. | | |
| 6,904,908 B2 | 6/2005 | Bruce et al. | | |
| 6,932,083 B2 | 8/2005 | Jones et al. | | |
| 6,934,220 B1 | 8/2005 | Cruitt et al. | | |
| 6,958,691 B1 | 10/2005 | Anderson et al. | | |
| 6,990,975 B1 | 1/2006 | Jones et al. | | |
| 7,009,517 B2 | 3/2006 | Wood | | |
| 7,072,738 B2 | 7/2006 | Bonney et al. | | |
| 7,089,786 B2 | 8/2006 | Walker | | |
| 7,091,864 B2 | 8/2006 | Veitch et al. | | |
| 7,151,456 B2 | 12/2006 | Godfrey | | |
| 7,159,533 B1 | 1/2007 | Redd et al. | | |
| 7,191,777 B2 | 3/2007 | Brand et al. | | |
| 7,198,172 B2 | 4/2007 | Harvey et al. | | |
| 7,233,228 B2 | 6/2007 | Lintell | | |
| 7,331,340 B2 | 2/2008 | Barney | | |
| 7,383,837 B2 | 6/2008 | Robertson et al. | | |
| 7,424,888 B2 | 9/2008 | Harvey et al. | | |
| 7,495,546 B2 | 2/2009 | Lintell | | |
| 7,597,099 B2 | 10/2009 | Jones et al. | | |
| 7,661,423 B2 | 2/2010 | Brand et al. | | |
| 7,730,847 B1 | 6/2010 | Redd et al. | | |
| 7,748,382 B2 | 7/2010 | Denyer et al. | | |
| 7,819,116 B2 | 10/2010 | Brand et al. | | |
| 7,837,648 B2 | 11/2010 | Blair et al. | | |
| 8,165,892 B2 | 4/2012 | Carter et al. | | |
| 8,261,738 B2 | 9/2012 | Denyer et al. | | |
| 8,403,861 B2 | 3/2013 | Williams et al. | | |
| 8,424,517 B2 | 4/2013 | Sutherland et al. | | |
| 8,464,707 B2 | 6/2013 | Jongejan et al. | | |
| 8,550,067 B2 | 10/2013 | Bruce et al. | | |
| 8,607,783 B2 | 12/2013 | Takei et al. | | |
| 8,807,131 B1 | 8/2014 | Tunnell et al. | | |
| 9,035,765 B2 | 5/2015 | Engelhard et al. | | |
| 9,072,846 B2 | 7/2015 | Helmlinger | | |
| 9,242,056 B2 | 1/2016 | Andersen et al. | | |
| D757,926 S | 5/2016 | Van Sickle et al. | | |
| 9,352,107 B2 | 5/2016 | Von Hollen et al. | | |
| 9,427,534 B2 | 8/2016 | Bruin et al. | | |
| 9,452,317 B2 | 9/2016 | Arkush | | |
| 9,468,729 B2 | 10/2016 | Sutherland et al. | | |
| D771,800 S | 11/2016 | Engelhard et al. | | |

(56) References Cited

U.S. PATENT DOCUMENTS

| | | | |
|---|---|---|---|
| 9,555,202 B2* | 1/2017 | Von Hollen | A61M 15/009 |
| 9,764,104 B2* | 9/2017 | Gumaste | A61M 11/005 |
| 9,782,551 B2 | 10/2017 | Morrison et al. | |
| 2002/0026935 A1* | 3/2002 | Schmidt | A61M 11/003 128/200.22 |
| 2002/0090601 A1 | 7/2002 | Strupat et al. | |
| 2002/0178783 A1* | 12/2002 | Miller | A61M 16/12 222/3 |
| 2003/0033055 A1* | 2/2003 | McRae | B05B 9/002 700/282 |
| 2003/0075171 A1 | 4/2003 | Jones et al. | |
| 2003/0079744 A1* | 5/2003 | Bonney | A61M 15/0043 128/203.12 |
| 2003/0159694 A1 | 8/2003 | McNaughton | |
| 2003/0234015 A1* | 12/2003 | Bruce | A61M 15/0016 128/200.23 |
| 2004/0007231 A1 | 1/2004 | Zhou | |
| 2004/0173209 A1* | 9/2004 | Grychowski | A61M 16/0833 128/200.14 |
| 2005/0005929 A1* | 1/2005 | Snyder | A61M 15/0086 128/200.23 |
| 2005/0081639 A1* | 4/2005 | Gourlay | A61B 5/087 73/718 |
| 2005/0087178 A1 | 4/2005 | Milton | |
| 2005/0092106 A1* | 5/2005 | Sheplak | G01F 15/024 73/862.623 |
| 2006/0089545 A1 | 4/2006 | Ratjen et al. | |
| 2007/0017506 A1 | 1/2007 | Bell et al. | |
| 2007/0125372 A1 | 6/2007 | Chen | |
| 2009/0056708 A1* | 3/2009 | Stenzler | A61M 11/08 128/200.14 |
| 2009/0095292 A1* | 4/2009 | Hamano | A61M 15/0085 128/203.14 |
| 2009/0194104 A1 | 8/2009 | Van Sickle | |
| 2009/0314292 A1 | 12/2009 | Overfield et al. | |
| 2010/0132699 A1* | 6/2010 | Burolla | A61M 15/00 128/200.23 |
| 2010/0191192 A1 | 7/2010 | Prasad et al. | |
| 2010/0192948 A1 | 8/2010 | Sutherland et al. | |
| 2010/0250280 A1 | 9/2010 | Sutherland | |
| 2010/0252036 A1 | 10/2010 | Sutherland et al. | |
| 2010/0324439 A1 | 12/2010 | Williams et al. | |
| 2011/0088690 A1* | 4/2011 | Djupesland | A61M 15/08 128/203.18 |
| 2011/0180563 A1 | 7/2011 | Fitchett et al. | |
| 2011/0226237 A1 | 9/2011 | Morrison | |
| 2011/0226242 A1 | 9/2011 | Von Hollen et al. | |
| 2012/0012106 A1 | 1/2012 | Bari | |
| 2012/0103326 A1* | 5/2012 | Karle | A61D 7/04 128/200.21 |
| 2012/0165693 A1 | 6/2012 | Williams et al. | |
| 2012/0190999 A1* | 7/2012 | Addington | A61M 15/00 600/538 |
| 2012/0240923 A1 | 9/2012 | Denyer et al. | |
| 2012/0285236 A1 | 11/2012 | Haartsen et al. | |
| 2012/0291779 A1 | 11/2012 | Haartsen et al. | |
| 2012/0312302 A1 | 12/2012 | Cardelius et al. | |
| 2012/0318265 A1* | 12/2012 | Amirav | A61M 15/00 128/203.29 |
| 2013/0008436 A1* | 1/2013 | Von Hollen | A61M 15/009 128/200.14 |
| 2013/0053719 A1 | 2/2013 | Wekell | |
| 2013/0092158 A1 | 4/2013 | Levy et al. | |
| 2013/0151162 A1 | 6/2013 | Harris et al. | |
| 2013/0186392 A1 | 7/2013 | Haartsen et al. | |
| 2013/0186393 A1* | 7/2013 | Von Hollen | A61M 16/208 128/200.23 |
| 2014/0000598 A1 | 1/2014 | Sutherland et al. | |
| 2014/0000599 A1 | 1/2014 | Dyche et al. | |
| 2014/0106324 A1 | 4/2014 | Adams et al. | |
| 2014/0182584 A1 | 7/2014 | Sutherland et al. | |
| 2014/0257126 A1 | 9/2014 | Vink et al. | |
| 2014/0318534 A1 | 10/2014 | Engelbreth | |
| 2014/0352690 A1 | 12/2014 | Kolb et al. | |
| 2015/0011906 A1 | 1/2015 | Wallach | |
| 2015/0059739 A1 | 3/2015 | Aslam | |
| 2015/0061867 A1 | 3/2015 | Engelhard et al. | |
| 2015/0099994 A1 | 4/2015 | Spencer et al. | |
| 2015/0100276 A1 | 4/2015 | Huang et al. | |
| 2015/0100335 A1 | 4/2015 | Engelhard et al. | |
| 2015/0112707 A1 | 4/2015 | Manice et al. | |
| 2015/0122261 A1 | 5/2015 | Pettit | |
| 2015/0164373 A1 | 6/2015 | Davis et al. | |
| 2015/0174348 A1 | 6/2015 | Tunnell et al. | |
| 2015/0174349 A1 | 6/2015 | Tunnell et al. | |
| 2015/0235548 A1 | 8/2015 | Engelhard et al. | |
| 2015/0273165 A1* | 10/2015 | Hadash | A61M 16/202 128/203.14 |
| 2015/0283337 A1 | 10/2015 | Adams et al. | |
| 2015/0283339 A1* | 10/2015 | Mahadevan | A61M 15/002 128/203.14 |
| 2015/0352281 A1 | 12/2015 | Pfragng | |
| 2016/0045681 A1 | 2/2016 | Cheatham, III et al. | |
| 2016/0045682 A1 | 2/2016 | Boyden et al. | |
| 2016/0045683 A1 | 2/2016 | Cheatham, III et al. | |
| 2016/0045685 A1 | 2/2016 | Hyde et al. | |
| 2016/0051776 A1 | 2/2016 | Von Hollen | |
| 2016/0058960 A1 | 3/2016 | Papania et al. | |
| 2016/0082208 A1 | 3/2016 | Ballam et al. | |
| 2016/0089507 A1* | 3/2016 | Dyche | A61M 11/005 128/200.22 |
| 2016/0106375 A1* | 4/2016 | Leydon | A61B 5/0871 600/538 |
| 2016/0106935 A1 | 4/2016 | Sezan et al. | |
| 2016/0129182 A1 | 5/2016 | Schuster et al. | |
| 2016/0129206 A1 | 5/2016 | Engelbreth | |
| 2016/0136366 A1 | 5/2016 | Bennett | |
| 2016/0136367 A1 | 5/2016 | Varney | |
| 2016/0144141 A1 | 5/2016 | Biwas et al. | |
| 2016/0144142 A1* | 5/2016 | Baker | A61M 15/008 128/200.23 |
| 2016/0148539 A1* | 5/2016 | Baker | G09B 23/28 434/262 |
| 2016/0166766 A1 | 6/2016 | Schuster et al. | |
| 2016/0184535 A1* | 6/2016 | Edwards | A61M 5/2046 604/111 |
| 2016/0193436 A1 | 7/2016 | Khasawneh | |
| 2016/0213865 A1* | 7/2016 | Poree | A61M 15/0065 |
| 2016/0213868 A1 | 7/2016 | Khasawneh et al. | |
| 2016/0256639 A1 | 9/2016 | Van Sickle et al. | |
| 2016/0287139 A1 | 10/2016 | Luttrell | |
| 2016/0314256 A1 | 10/2016 | Su et al. | |
| 2016/0325058 A1 | 11/2016 | Samson et al. | |
| 2016/0331917 A1 | 11/2016 | Bennett et al. | |
| 2016/0339187 A1* | 11/2016 | Smaldone | A61M 11/06 |
| 2016/0339190 A1* | 11/2016 | Morrison | A61B 5/4833 |
| 2016/0354562 A1* | 12/2016 | Morrison | G08B 5/36 |
| 2017/0020776 A1 | 1/2017 | Khasawneh et al. | |
| 2017/0079557 A1* | 3/2017 | Lauk | A61B 5/74 |
| 2017/0087313 A1* | 3/2017 | Rosenfeld | A61M 15/0013 |
| 2017/0127945 A1 | 5/2017 | Reed | |
| 2017/0173282 A1 | 6/2017 | O'Sullivan et al. | |
| 2017/0333645 A1* | 11/2017 | Alizoti | A61M 15/0086 |
| 2017/0333661 A1* | 11/2017 | Bennett | A61M 16/0866 |
| 2018/0008790 A1* | 1/2018 | Costella | A61B 5/0876 |
| 2019/0046079 A1* | 2/2019 | Reed | A61M 15/0021 |
| 2019/0160237 A1* | 5/2019 | O'Callaghan | A61B 5/4839 |
| 2019/0366018 A1* | 12/2019 | Conlon | A61M 15/0021 |
| 2020/0001026 A1* | 1/2020 | Starr | A61M 15/009 |

FOREIGN PATENT DOCUMENTS

| | | | |
|---|---|---|---|
| EP | 0387222 B1 | 7/1993 | |
| EP | 0824023 A1 | 2/1998 | |
| EP | 0617628 B1 | 5/1998 | |
| EP | 1338296 A1 | 8/2003 | |
| EP | 1330283 B1 | 9/2006 | |
| EP | 1745816 A2 * | 1/2007 | A61M 11/002 |
| EP | 1993642 B1 | 1/2012 | |
| EP | 1670533 B1 | 7/2012 | |
| EP | 2300083 B1 | 5/2013 | |

(56) References Cited

FOREIGN PATENT DOCUMENTS

| | | |
|---|---|---|
| EP | 2609954 A2 | 7/2013 |
| EP | 2376156 B1 | 1/2014 |
| EP | 2859906 A1 | 4/2015 |
| EP | 2563436 B1 | 10/2015 |
| EP | 2512566 B1 | 5/2016 |
| EP | 1613214 B1 | 10/2016 |
| EP | 3053620 A3 | 10/2016 |
| EP | 3097937 A1 | 11/2016 |
| GB | 2406283 A | 3/2005 |
| GB | 2479953 A | 2/2011 |
| GB | 2490770 A | 11/2012 |
| GB | 2512047 A | 9/2014 |
| GB | 2479953 B | 4/2015 |
| JP | 2006015793 A * | 1/2006 ......... B60C 23/0494 |
| WO | WO 1990/10470 A1 | 9/1990 |
| WO | WO 1992/07599 A1 | 5/1992 |
| WO | WO 1993/12823 A2 | 7/1993 |
| WO | WO 1995/07723 A1 | 2/1995 |
| WO | WO 1995/22365 A1 | 8/1995 |
| WO | WO 1997/29799 A2 | 8/1997 |
| WO | WO97/48293 | 12/1997 |
| WO | WO 1999/11310 A1 | 3/1999 |
| WO | WO 2002/05879 A1 | 1/2002 |
| WO | WO 2002/09574 A2 | 2/2002 |
| WO | WO 2002/058771 A1 | 8/2002 |
| WO | WO 2003/020349 A2 | 3/2003 |
| WO | WO 2003/063937 A1 | 8/2003 |
| WO | WO 2003/092576 A2 | 11/2003 |
| WO | WO 2003/107523 A1 | 12/2003 |
| WO | WO 2005/042076 A1 | 5/2005 |
| WO | WO 2005/074455 A2 | 8/2005 |
| WO | WO 2006/123956 A1 | 11/2006 |
| WO | WO 2007/101438 A1 | 9/2007 |
| WO | WO 2008112353 A2 | 9/2008 |
| WO | WO 2009/022139 A1 | 2/2009 |
| WO | WO 2010/023591 A2 | 3/2010 |
| WO | WO 2010/023591 A3 | 3/2010 |
| WO | WO 2010/110682 A1 | 9/2010 |
| WO | WO 2010/114392 A1 | 10/2010 |
| WO | WO 2011/003017 A1 | 1/2011 |
| WO | WO 2011/073806 A1 | 6/2011 |
| WO | WO 2011/083377 A1 | 7/2011 |
| WO | WO 2011//089486 A1 | 7/2011 |
| WO | WO 2011/089489 A1 | 7/2011 |
| WO | WO 2011/089490 A1 | 7/2011 |
| WO | WO 2011/130183 A2 | 10/2011 |
| WO | WO 2011/130583 A2 | 10/2011 |
| WO | WO 2011/135353 A1 | 11/2011 |
| WO | WO 2012/038861 A1 | 3/2012 |
| WO | WO 2012/064540 A2 | 5/2012 |
| WO | WO 2012/173992 A1 | 12/2012 |
| WO | WO 2013/028705 A2 | 2/2013 |
| WO | WO 2013/042002 A1 | 3/2013 |
| WO | WO 2013/043063 A1 | 3/2013 |
| WO | WO 2013/061240 A1 | 5/2013 |
| WO | WO 2013/061248 A1 | 5/2013 |
| WO | WO 2013/098334 A1 | 7/2013 |
| WO | WO 2013/124624 A1 | 8/2013 |
| WO | WO 2014/004437 A1 | 1/2014 |
| WO | WO 2014/033229 A1 | 3/2014 |
| WO | WO 2014/147550 A1 | 9/2014 |
| WO | WO 2014/202923 A1 | 12/2014 |
| WO | WO 2014/204511 A3 | 12/2014 |
| WO | WO 2015/002651 A1 | 1/2015 |
| WO | WO 2015/004554 A1 | 1/2015 |
| WO | WO 2015/004559 A2 | 1/2015 |
| WO | WO 2015/006701 A2 | 1/2015 |
| WO | WO 2015/008013 A1 | 1/2015 |
| WO | WO 2015/022595 A1 | 2/2015 |
| WO | WO 2015/030610 A2 | 3/2015 |
| WO | WO 2015/031472 A1 | 3/2015 |
| WO | WO 2015/036010 A3 | 3/2015 |
| WO | WO 2015/036723 A1 | 3/2015 |
| WO | WO 2015/052519 A1 | 4/2015 |
| WO | WO 2015/104522 A1 | 7/2015 |
| WO | WO 2015/109259 A1 | 7/2015 |
| WO | WO 2015/114285 A1 | 8/2015 |
| WO | WO 2015/128173 A1 | 9/2015 |
| WO | WO 2015/133909 A1 | 9/2015 |
| WO | WO 2015/138454 A1 | 9/2015 |
| WO | WO 2015/144442 A1 | 10/2015 |
| WO | WO 2015/150029 A1 | 10/2015 |
| WO | WO 2015/154864 A2 | 10/2015 |
| WO | WO 2015/154865 A2 | 10/2015 |
| WO | WO 2015/174856 A1 | 11/2015 |
| WO | WO 2015/178907 A1 | 11/2015 |
| WO | WO 2016/174856 A1 | 11/2015 |
| WO | WO 2016/025553 A1 | 2/2016 |
| WO | WO 2016/030521 A1 | 3/2016 |
| WO | WO 2016/033419 A1 | 3/2016 |
| WO | WO 2016/033421 A1 | 3/2016 |
| WO | WO 2016/043601 A1 | 3/2016 |
| WO | WO 2016/048435 A1 | 3/2016 |
| WO | WO 2016/049066 A1 | 3/2016 |
| WO | WO 2016/060863 A3 | 4/2016 |
| WO | WO 2016/075525 A1 | 5/2016 |
| WO | WO 2016/079461 A1 | 5/2016 |
| WO | WO 2016/081294 A1 | 5/2016 |
| WO | WO 2016/085988 A2 | 6/2016 |
| WO | WO 20160920260 A1 | 6/2016 |
| WO | WO 2016/110804 A1 | 7/2016 |
| WO | WO 2016/111633 A1 | 7/2016 |
| WO | WO 2016/116591 A1 | 7/2016 |
| WO | WO 2016/162699 A1 | 10/2016 |
| WO | WO 2016/165029 A1 | 10/2016 |
| WO | WO 2016/181048 A1 | 11/2016 |
| WO | WO 2017/071879 A1 | 5/2017 |
| WO | WO 2017/178776 A1 | 10/2017 |
| WO | WO 2017/187116 A1 | 11/2017 |
| WO | WO 2017/194906 A1 | 11/2017 |
| WO | WO-2018203188 A1 * | 11/2018 ......... A61M 16/0006 |
| WO | WO 2021/255202 A1 | 12/2021 |

OTHER PUBLICATIONS

Written Opinion of the International Search Report and Written Opinion of the International Searching Authority in International Application No. PCT/IB2017/055603 dated Jan. 5, 2018, 10 pages.
PCT Notification of the International Search Report and Written Opinion of the International Searching Authority in International Application No. PCT/IB2017/055603 dated Jan. 5, 2018, 10 pages.
Japanese Office Action for Patent Application No. 2018-549838 dated Mar. 14, 2022.

* cited by examiner

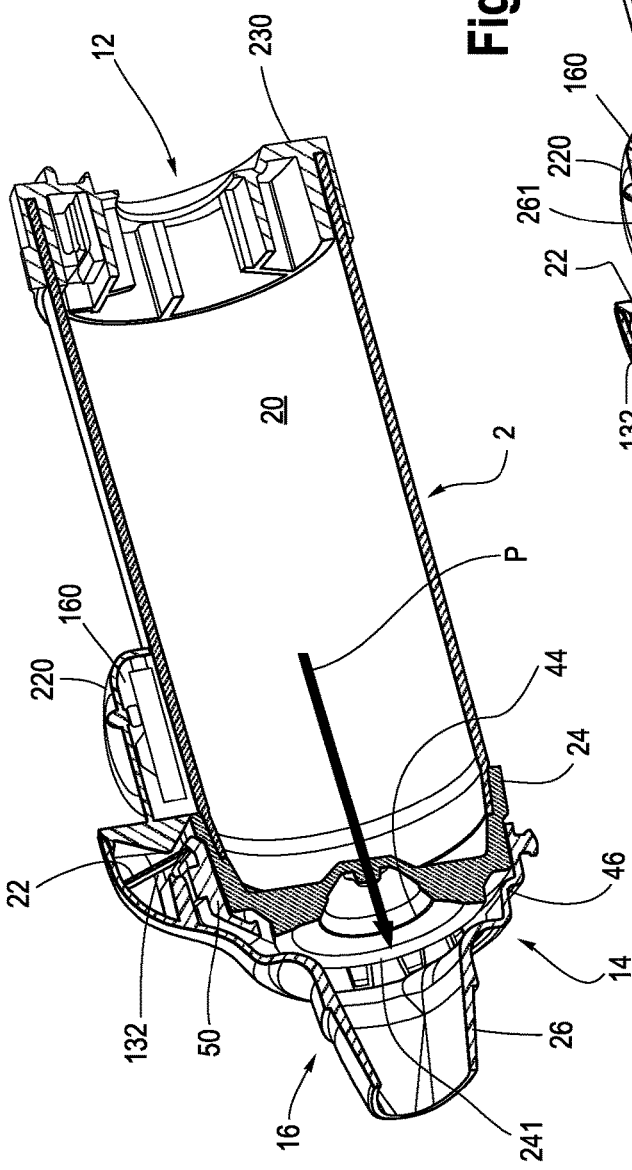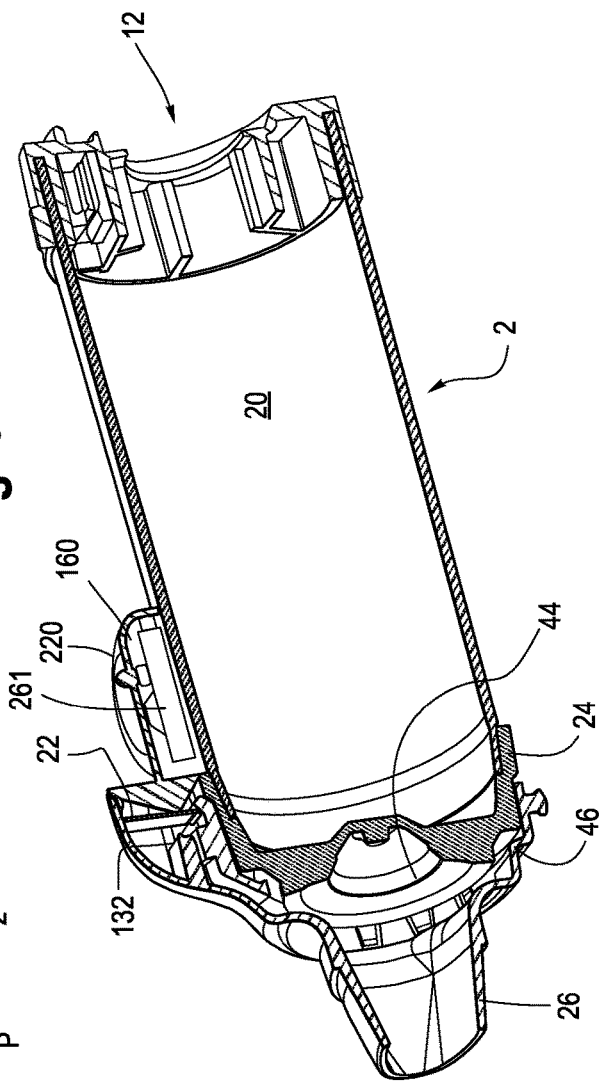

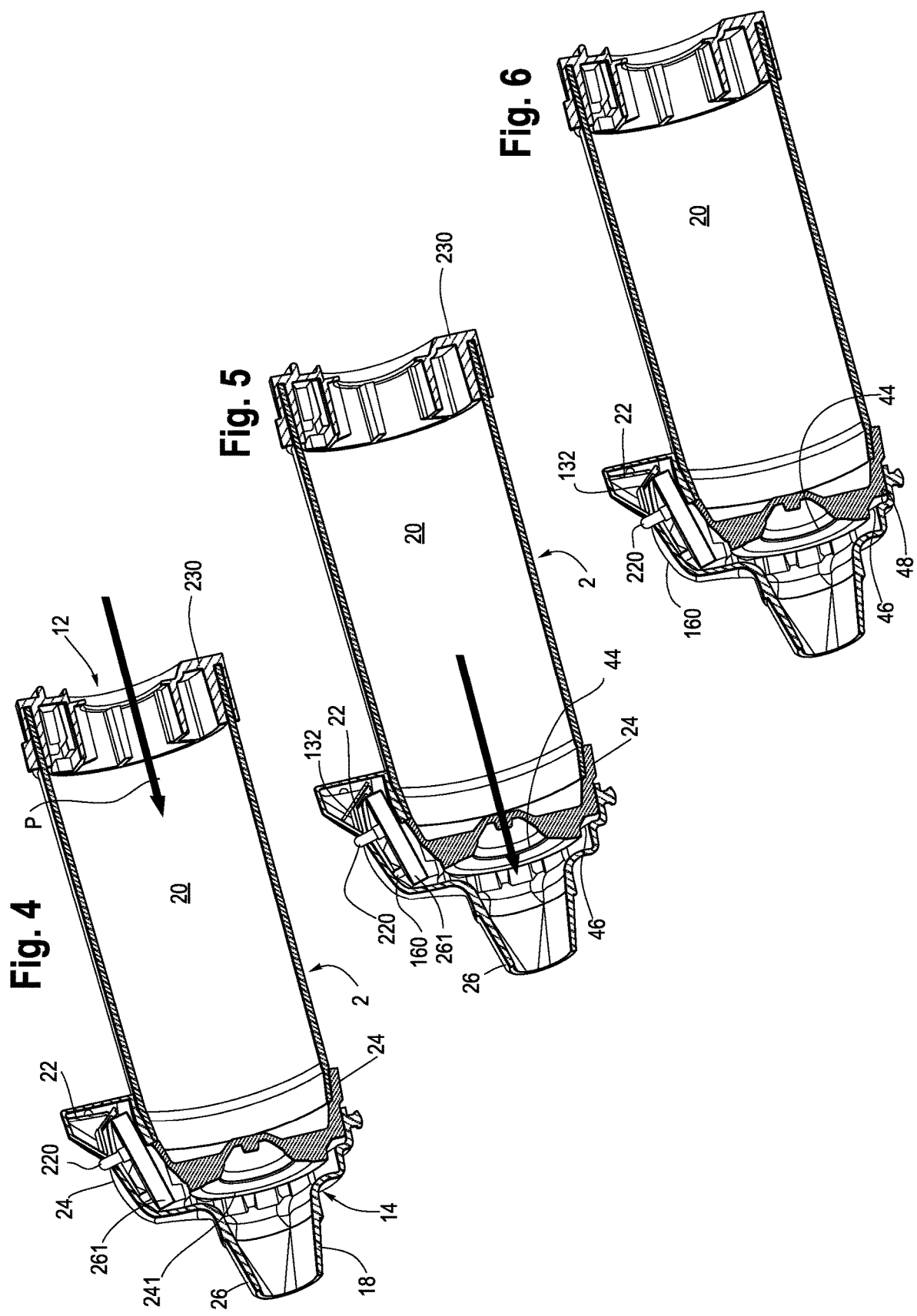

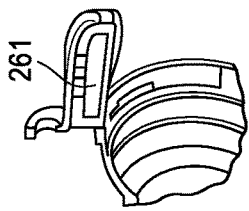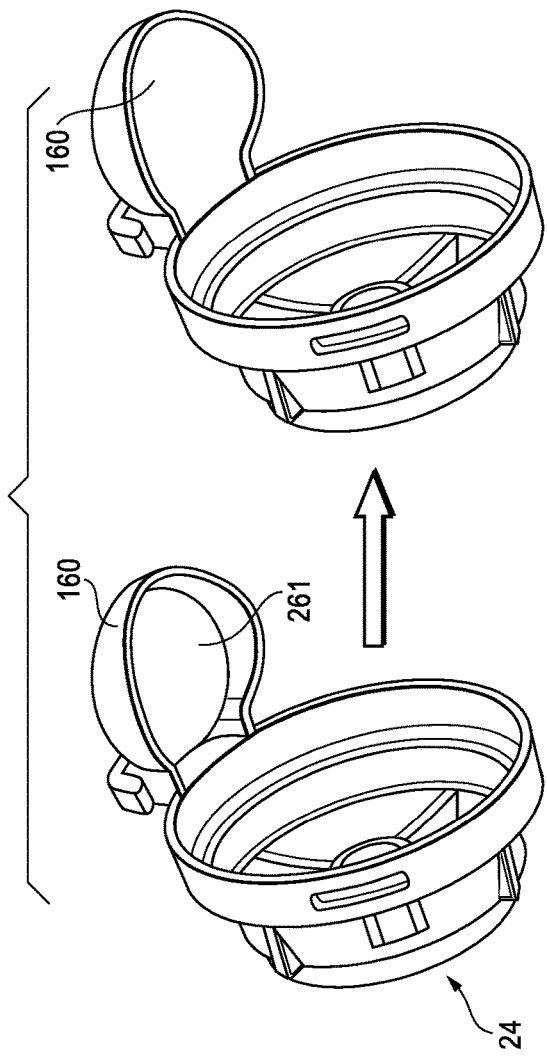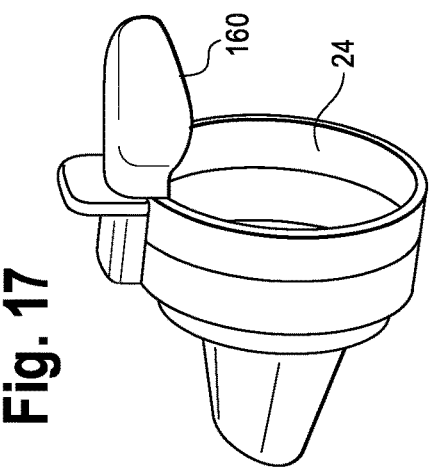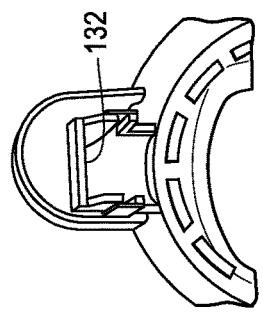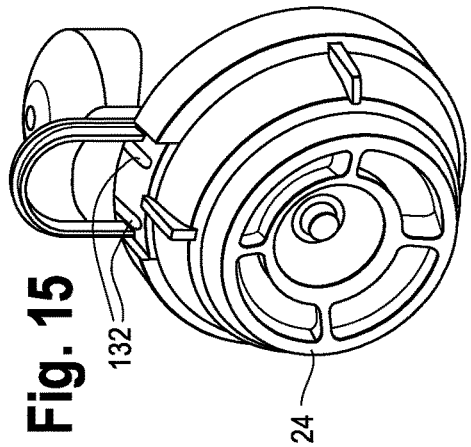

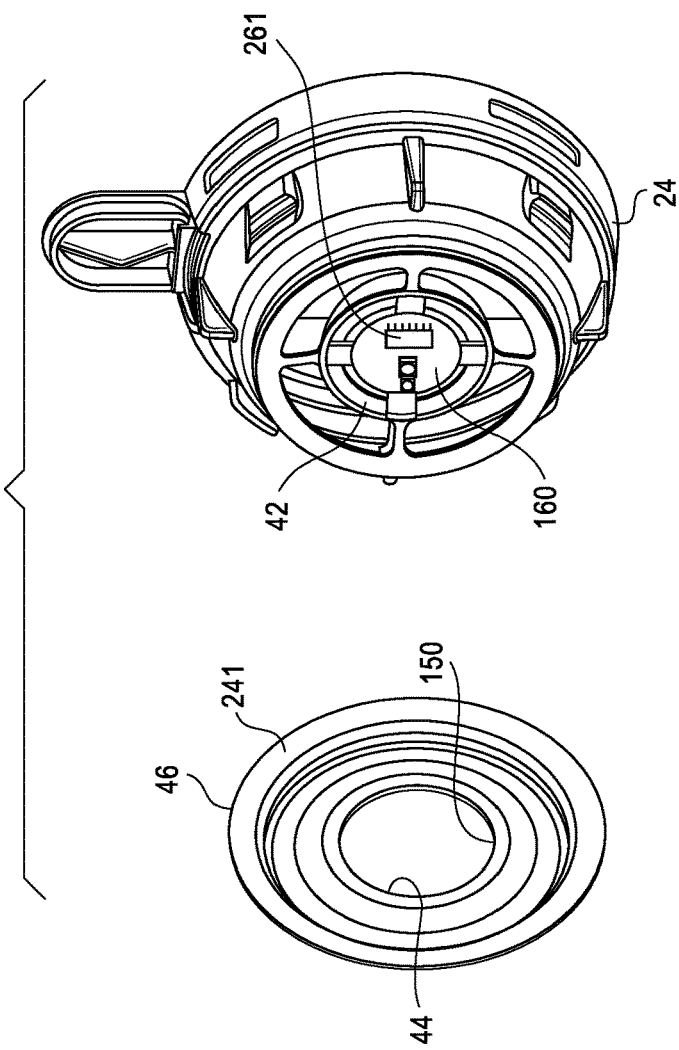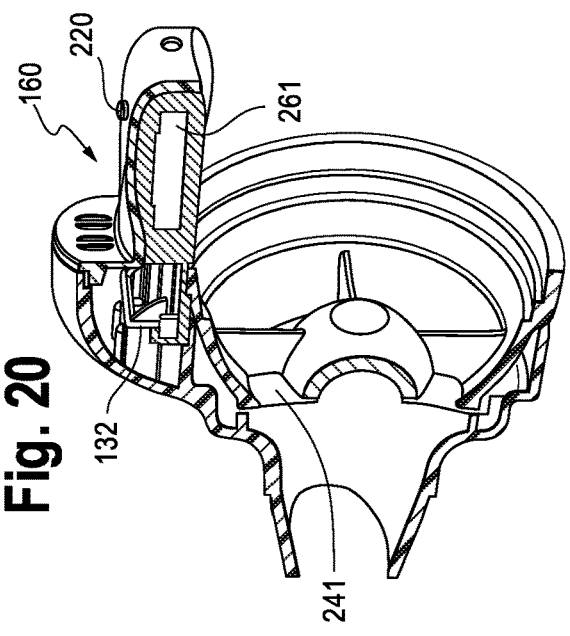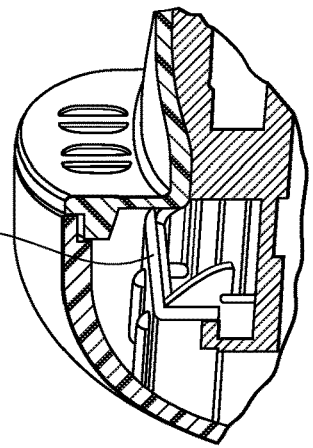

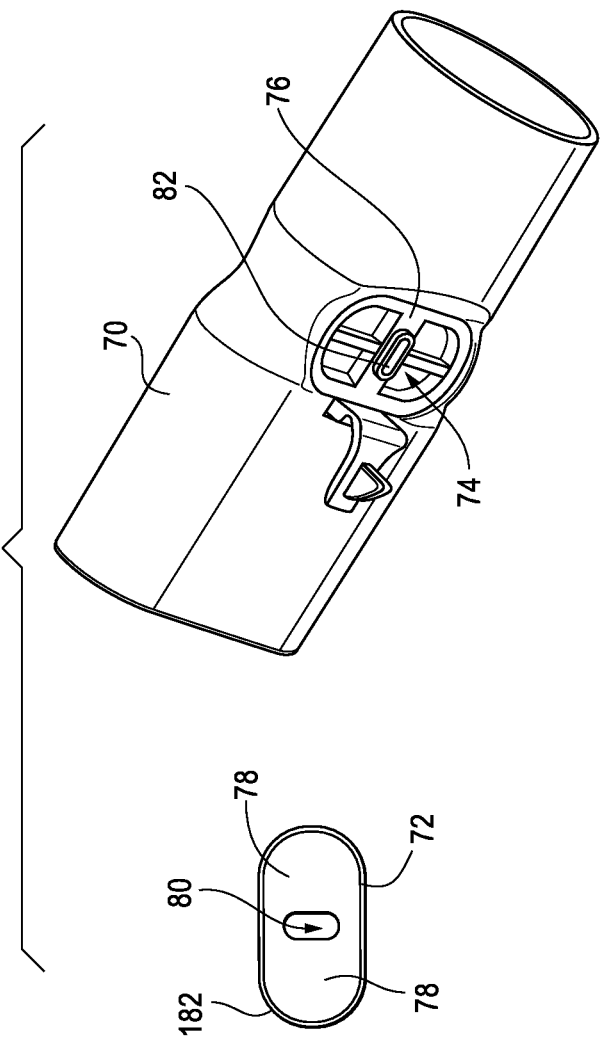
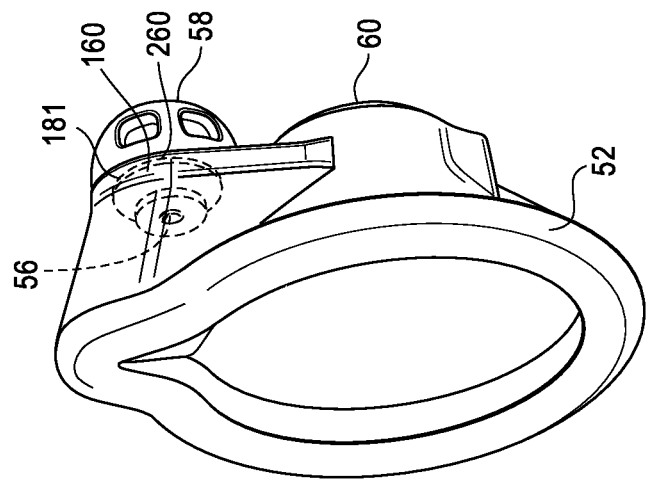

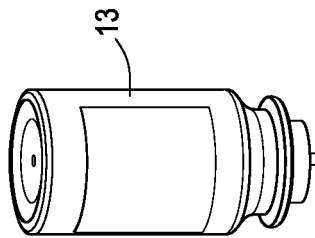
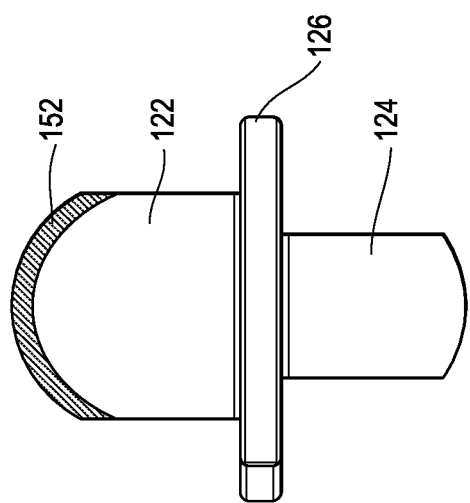
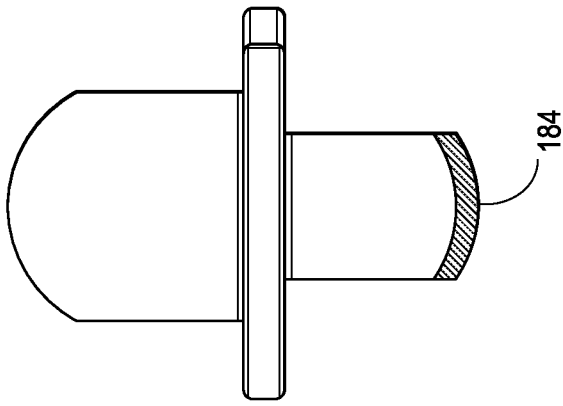
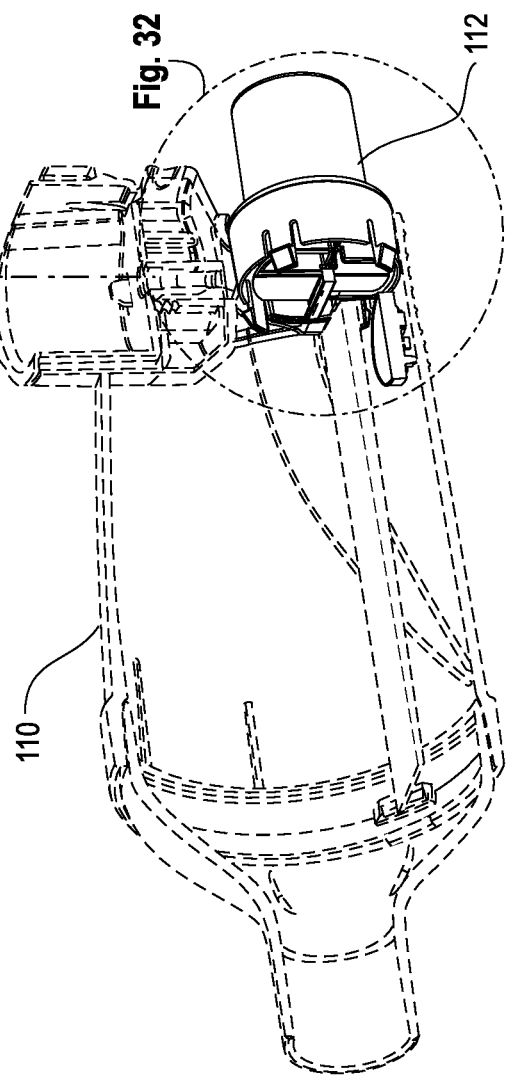

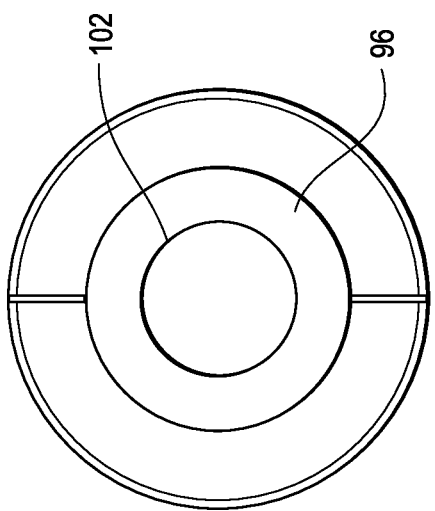
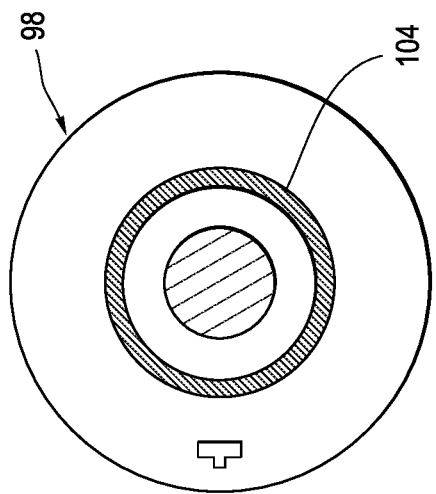
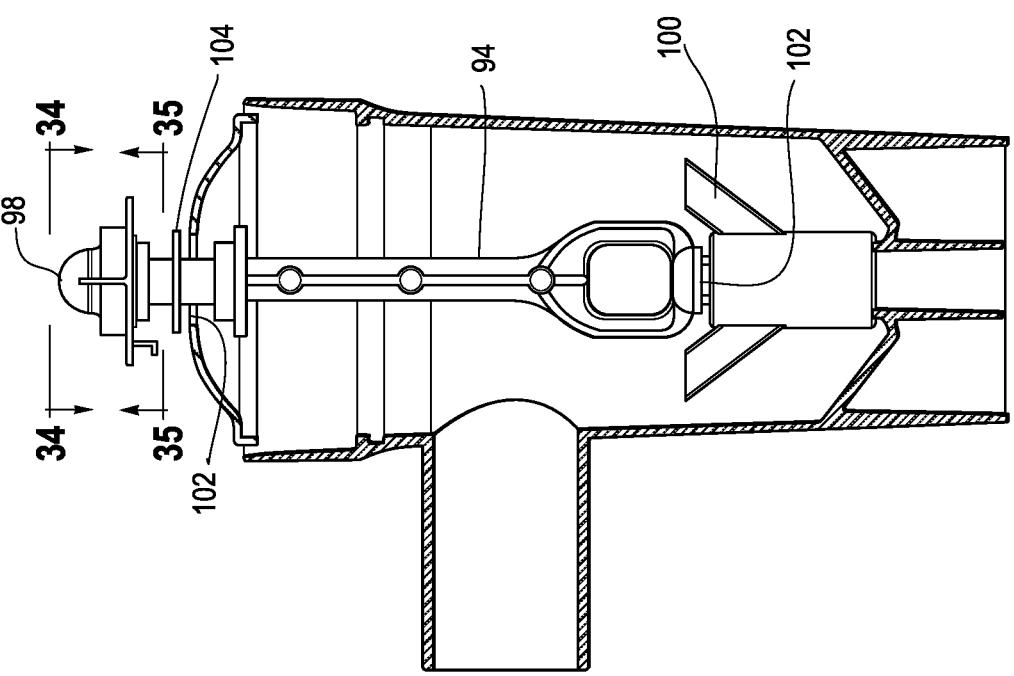

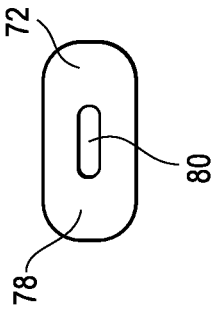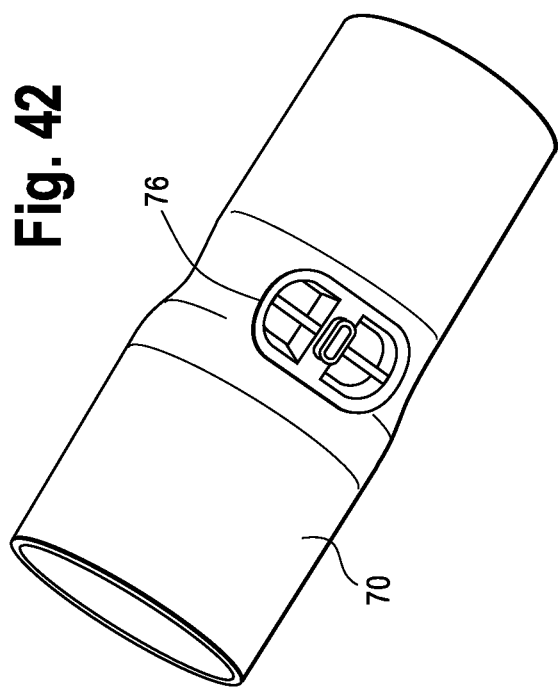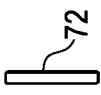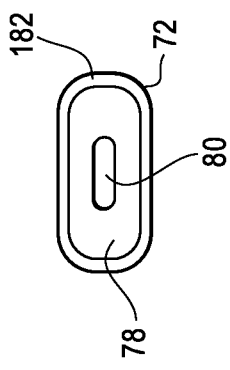

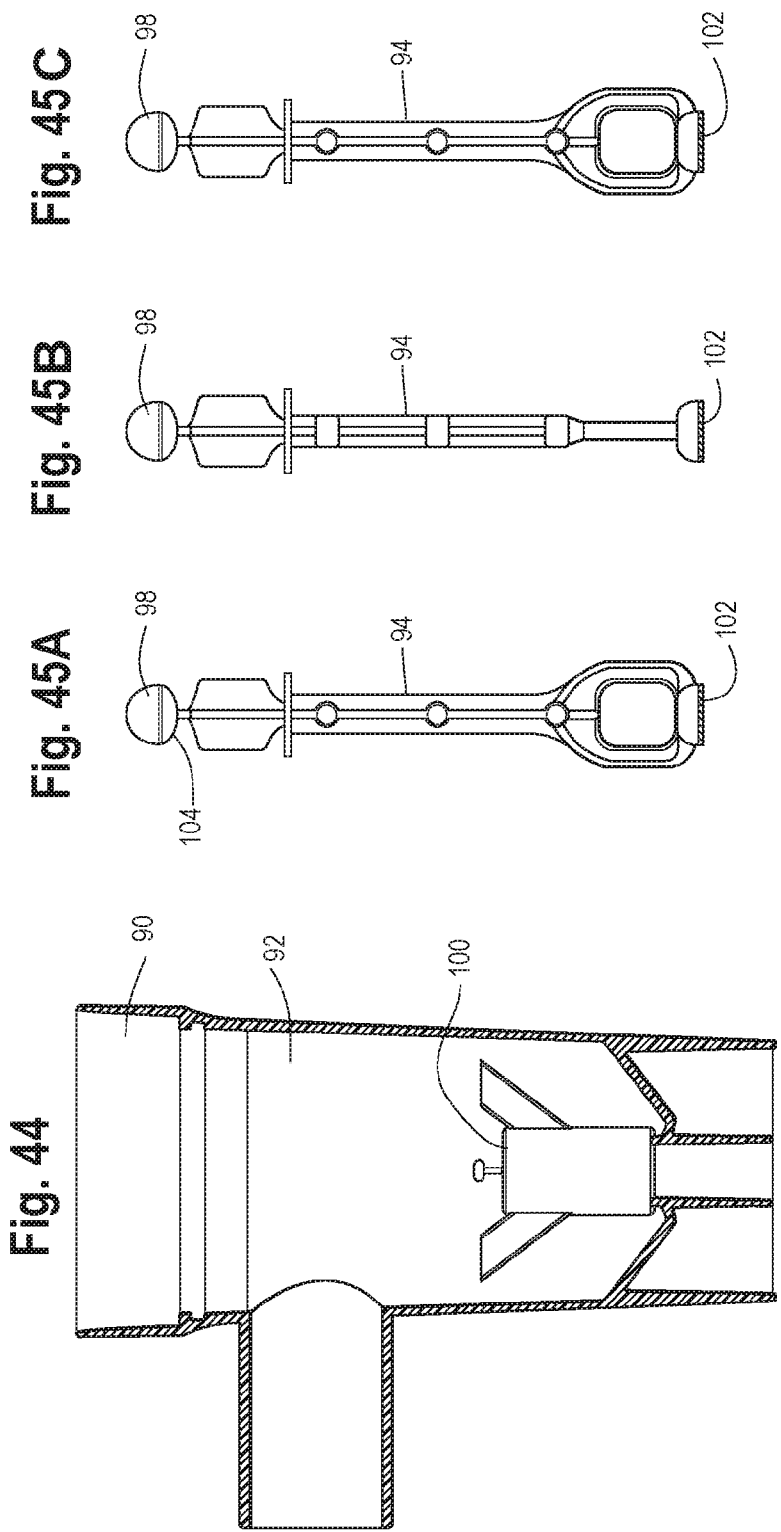

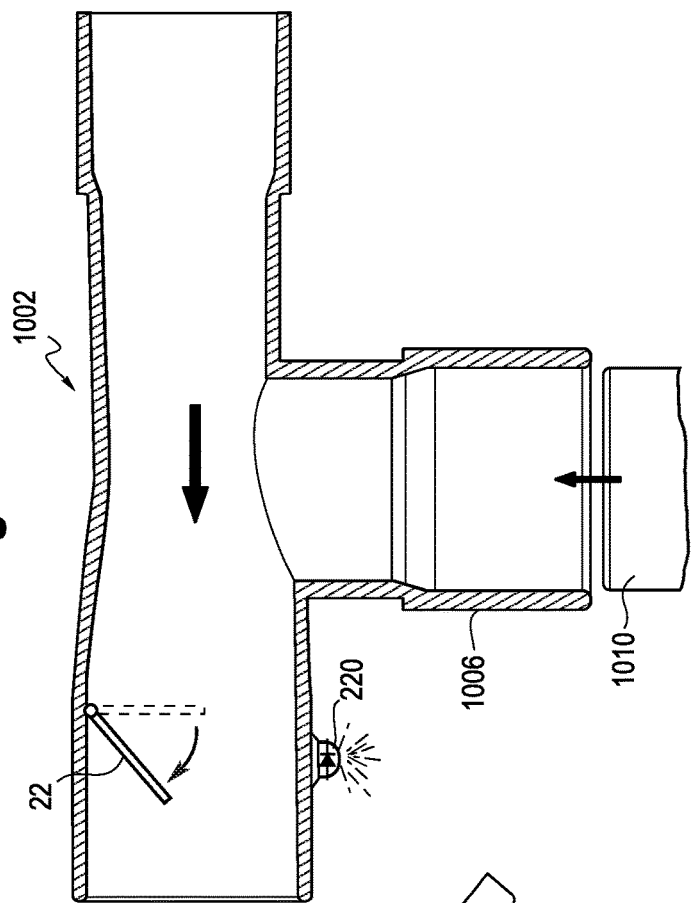
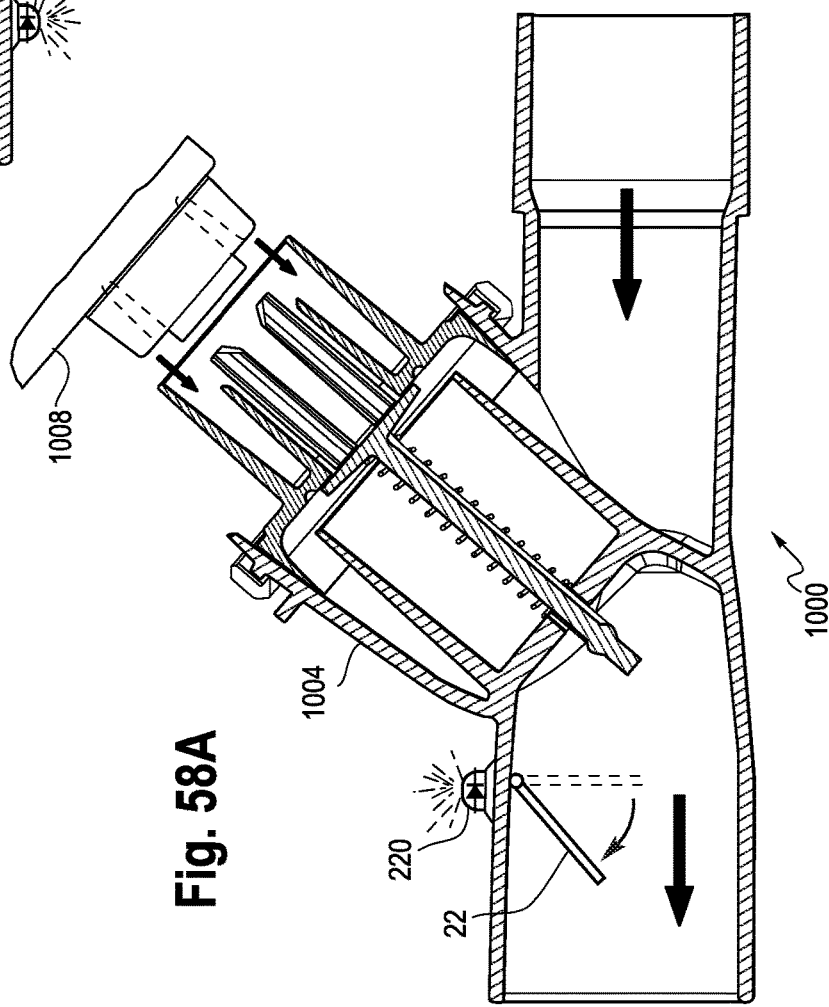

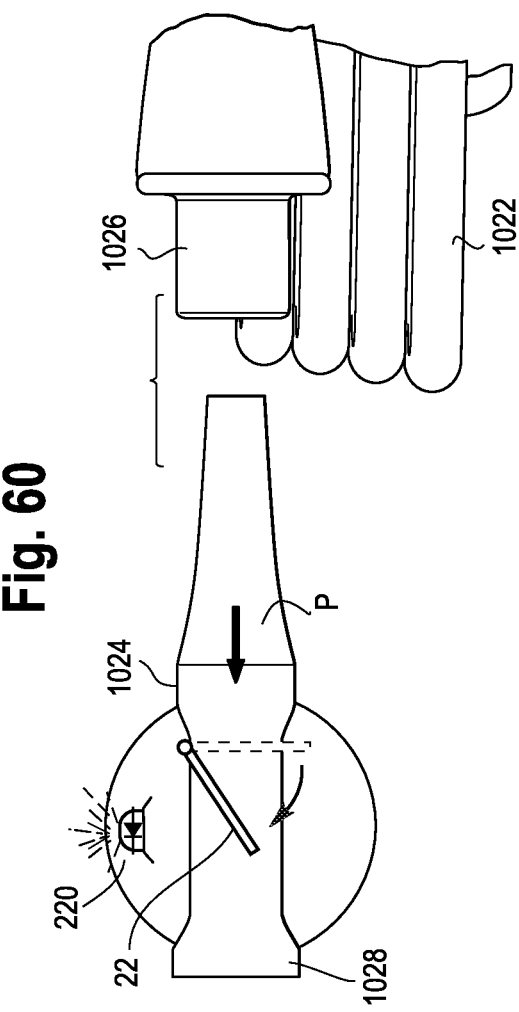
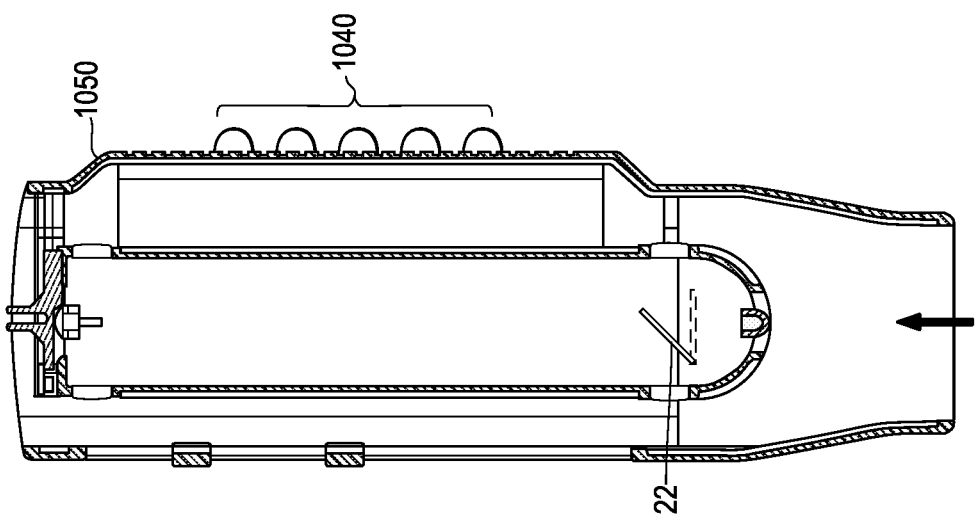

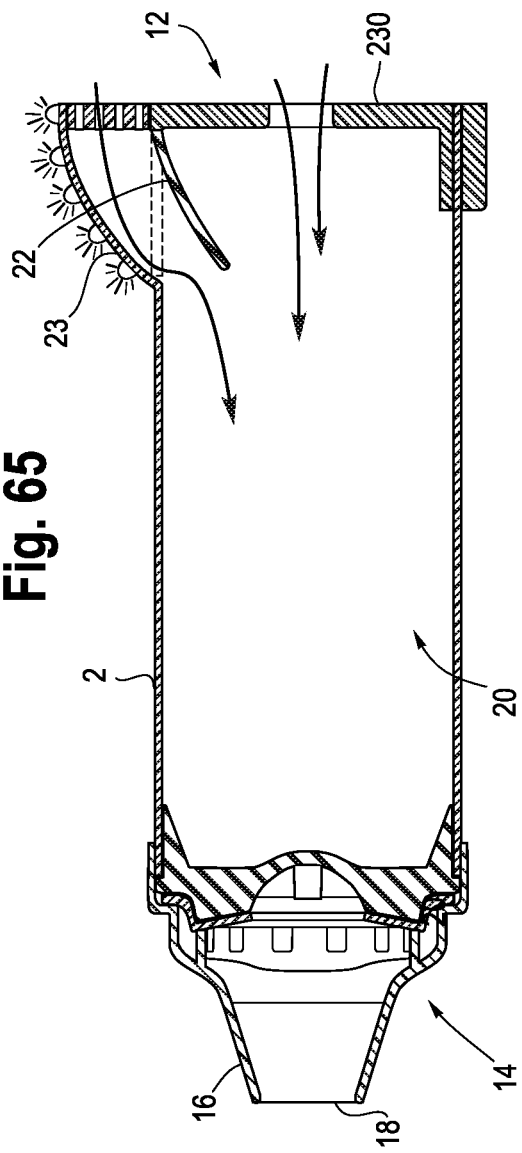
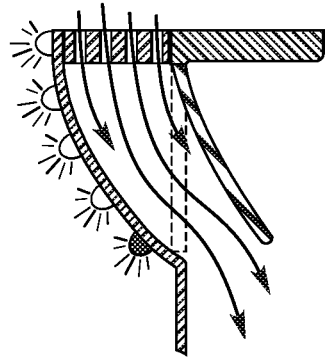
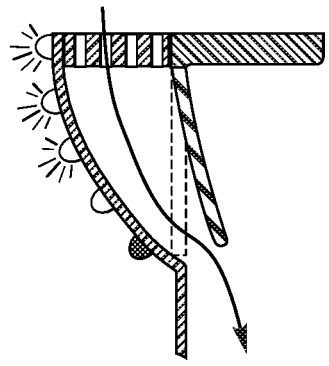
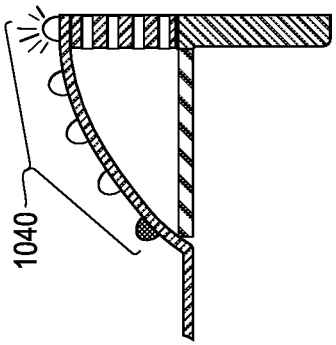

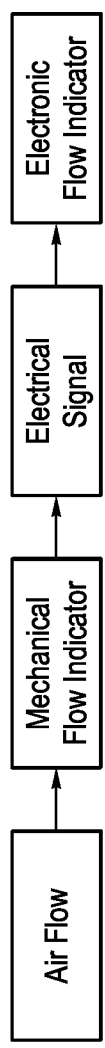
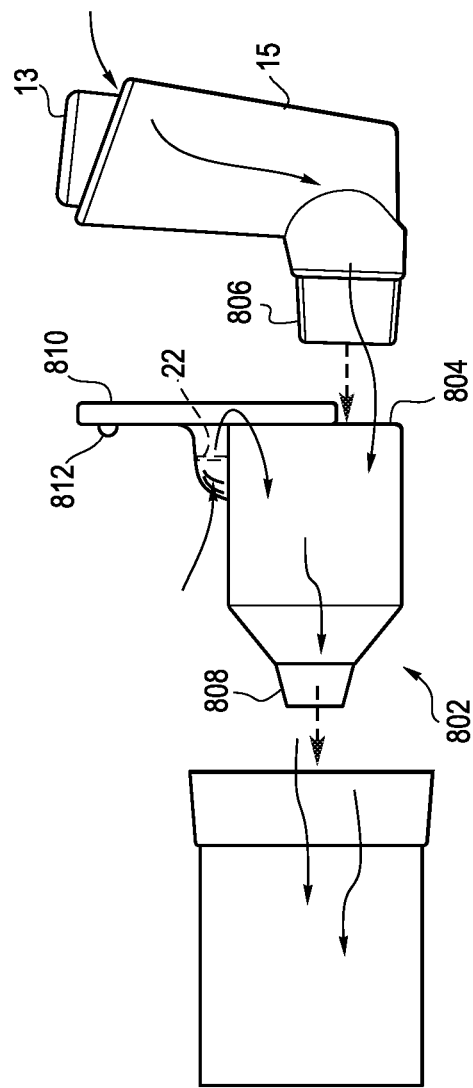

RESPIRATORY CARE SYSTEM WITH ELECTRONIC INDICATOR

This application is a continuation of U.S. application Ser. No. 15/467,450, filed Mar. 23, 2017 and entitled "Respiratory Care System With Electronic Indicator," now U.S. Pat. No. 10,894,142, which application claims the benefit of U.S. Provisional Application 62/337,626, filed May 17, 2016 and entitled "Respiratory Care System With Electronic Indicator," U.S. Provisional Application No. 62/312,830, filed Mar. 24, 2016 and entitled "Medicament Delivery System With Electronic Indicator," and U.S. Provisional Application 62/465,479, filed Mar. 1, 2017 and entitled "Smart Metered Dose Inhaler Applicator," the entire disclosures of which are hereby incorporated herein by reference.

TECHNICAL FIELD

The present invention relates generally to a respiratory care system, and in particular, to a medicament delivery device, an accessory device to a medicament delivery device, or respiratory exercise device, each configured with an electronic indicator, which may provide visual, auditory or tactile feedback to a user or caregiver of inhalation, exhalation, and/or completion of a respiratory cycle, as well as end of life information for the system or device.

BACKGROUND

Individuals suffering from asthma, COPD or other respiratory ailments may require medication delivered in aerosol form for inhalation into the lungs for treating or preventing the respiratory ailment. In some cases, medication is administered in aerosol form from a nebulizer, catheter, dry powder inhaler (DPI), or metered dose inhaler (MDI). Patients suffering from respiratory ailments may also benefit from using respiratory exercise devices, such as oscillating expiratory pressure devices.

MDIs require the user to time their inhalation corresponding to actuation of the MDI, which may be difficult for some users, specifically children. Poor coordination may lead to medication being deposited in the mouth or throat rather than the lungs. To improve drug delivery from MDIs, an accessory device, such as a valved holding chamber (VHC), may be used to suspend the medication dispensed from the MDI in the chamber until the user inhales. While a VHC aids in proper drug delivery from MDIs, the VHC may be enhanced by further indicating to the user that, for example, inhalation is successful. Such feedback may provide the user, whether a patient or caregiver, confidence that the patient is properly using the MDI and VHC and, thus, receiving the required medication. Electronic MDIs that provide feedback to a user or caregiver regarding the proper use of the MDI are known in the art. These MDIs are typically quite expensive.

While various devices may provide features that indicate to the user that inhalation and/or exhalation is being achieved, often the indicator is positioned within a chamber or other component housing, and may be difficult to observe due to humidity or moisture buildup during treatment. In addition, many devices are not able to provide an indication that a successful treatment was completed. For example, while information about flow is important, such indicators often do not provide information about whether all of the medication was properly delivered.

In addition, many of the known devices have chambers that may degrade over time due to material/coating degradation and the like, which may lead to users continuing treatment with VHCs beyond a recommended time period.

SUMMARY

A medication delivery system includes a user interface, A flow indicator is moveable in response to inhalation and/or exhalation, or both, by a user through the user interface. An electronic indicator is operable in response to an electronic signal transmitted in response to the movement of the flow indicator. Methods of use and assembly are also provided. In some embodiments, the flow indicator may also be an inhalation valve, exhalation valve or actuator. By using a VHC with electronic indicator capability as described herein, a user or caregiver is able to use a less expensive mechanical MDI without electronic indicia capability. Other types of accessory devices with feedback indicia may also be used as training tools to teach and promote proper usage techniques with medicament delivery devices.

In one embodiment, a medication delivery system includes a holding chamber having an input end, an output end having a user interface having an outlet and an interior volume of space defined between the input and output ends, and a flow indicator. The flow indicator is moveable in response to inhalation and/or exhalation by a user through the user interface. In some embodiments, the flow indicator is a mechanical flow indicator. An electronic indicator is operable in response to an electronic signal transmitted in response to the movement of the flow indicator. Methods of use and assembly are also provided.

The various aspects and embodiments provide significant advantages relative to the prior known devices. For example, in one embodiment, the holding chamber may be used with an MDI, or other medicament delivery devices, such as a dry powder inhaler or nebulizer, and/or respiratory exercise devices, such as a PEP device or OPEP device, with an indicator providing electronic feedback, for example and without limitation by way of visual feedback via LED, as to when sufficient inhalation is achieved and/or when all of the drug has been inhaled and treatment is complete. The flow indicator may be incorporated for mechanical feedback, with movement between first and second positions indicating that inhalation is sufficient. The electronic components may be integrated in the assembly of the device, or embodied in a modular component that may be fitted or connected to existing valved holding chambers or other medicament delivery systems and/or respiratory exercise systems.

BRIEF DESCRIPTION OF THE DRAWINGS

The Figures show different embodiments of the medication delivery system, block/flow diagrams and methods for use and assembly thereof.

FIG. 2 is a cross-sectional view of the valved holding chamber s shown in FIG. 1 with the inhalation valve in an open position, the flow indicator in an operable position and the electronic indicator indicating proper inhalation.

FIG. 3 is a cross-sectional view of the valved holding chamber shown in FIG. 1 with an electronic indicator indicating an end of life for the valved holding chamber.

FIG. 4 is a cross-sectional view of a second embodiment of a valved holding chamber with an inhalation valve in a closed position and a flow indicator in a neutral position.

FIG. 5 is a cross-sectional view of the valved holding chamber shown in FIG. 3 with the inhalation valve in an open position and the flow indicator in an operable position and the electronic indicator indicating proper inhalation.

FIG. 6 is a cross-sectional view of the valved holding chamber shown in FIG. 1 with an electronic indicator indicating an end of life for the valved holding chamber.

FIG. 13 is a perspective view of releasable end assembly for a valve holding chamber having a flow indicator and an electronic indicator.

FIG. 14 is a partial cross-sectional view of the end assembly shown in FIG. 13.

FIG. 15 is a front perspective view of the end assembly shown in FIG. 13.

FIG. 16 is an enlarged, partial view of the end assembly with the flow indicator removed.

FIG. 17 is perspective view of the end assembly shown in FIG. 13 with a patient interface secured thereto.

FIG. 20 is a cut-away view of an end assembly with an electronic flow indicator.

FIG. 21 is an enlarged view of the end assembly shown in FIG. 20.

FIG. 22 is an exploded view of an end assembly having a valve.

FIG. 25 is a perspective view of the mask assembly of FIG. 24.

FIG. 26 is an exploded view of a mouthpiece having a valve.

FIGS. 30A and B are opposite views of a combined inhalation/exhalation valve.

FIG. 31 is a cross-sectional view of a medicament delivery device incorporating the valve shown in FIGS. 30A and B.

FIG. 33 is a side view of a nebulizer.

FIG. 34 is a top view of a diaphragm.

FIG. 35 is a bottom view of a dial.

FIG. 42 is a perspective view of a mouthpiece.

FIGS. 43A-C are front, side and rear views of a valve incorporated into the mouthpiece shown in FIG. 42.

FIG. 44 is a side view of a nebulizer.

FIGS. 45A-C are front, side and rear views of a nebulizer actuator incorporated into the nebulizer of FIG. 44.

FIGS. 58A and B are partial cross-sectional views of medication delivery adapter for use in a ventilator system.

FIG. 60 is an exploded view of tubing and an indicator.

FIG. 61 is a schematic cross-sectional view of a peak flow meter.

FIG. 65 is a cross-sectional view of another embodiment of a valved holding chamber.

FIGS. 66A-C are enlarged, partial cross-sectional views of the mechanical flow indicator and an array of electronic indicators.

FIG. 67 is a flow chart illustrating the sequence of flow detection and corresponding indication thereof.

FIG. 68 is a side view of metered dose inhaler adapter being applied to a valved holding chamber.

DETAILED DESCRIPTION OF THE DRAWINGS

Figure 1:
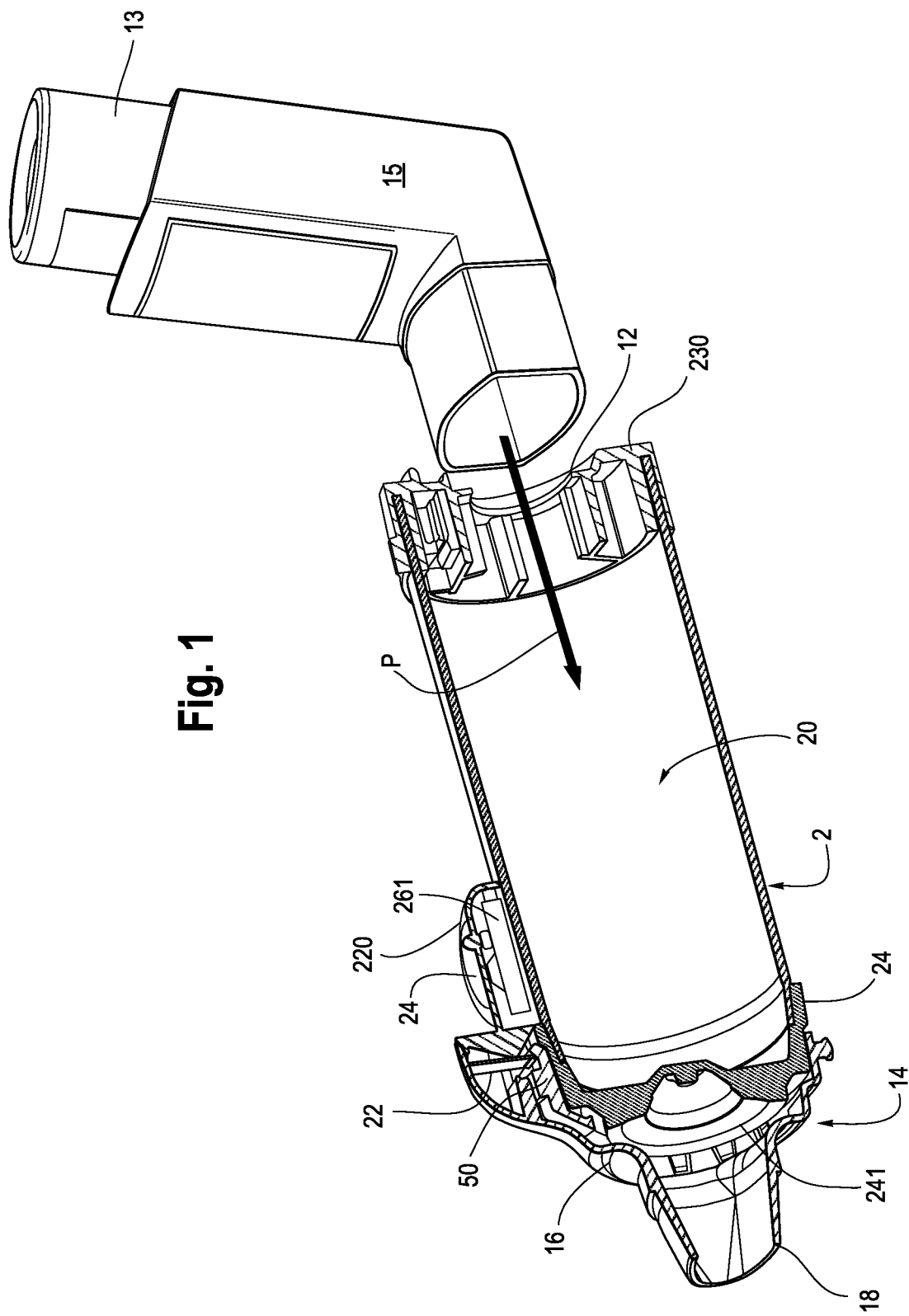
FIG. 1 is a cross-sectional view of a first embodiment of a valved holding chamber with an inhalation valve in a closed position and a flow indicator in a neutral position.

It should be understood that the term "plurality," as used herein, means two or more. The term "coupled" means connected to or engaged with, whether directly or indirectly, for example with an intervening member, and does not require the engagement to be fixed or permanent, although it may be fixed or permanent. It should be understood that the use of numerical terms "first," "second," "third," etc., as used herein does not refer to any particular sequence or order of components; for example "first" and "second" ring-like housing components may refer to any sequence of such members, and is not limited to the first and second ring-like housing components of a particular configuration unless otherwise specified. As used herein, "respiratory care system" includes any one or more of a medicament delivery device, an accessory device to a medicament delivery device, and respiratory exercise device.

Referring to the drawings, the various medicament delivery systems include a valved holding chamber 2 having an input end 12, an output end 14 having a user interface 16 with an outlet 18 and an interior volume 20 of space defined between the input and output ends. A flow indicator 22 is moveable in response to inhalation and/or exhalation by a user through the outlet. An electronic indicator 220 is operable in response to an electronic signal transmitted in response to the movement of the flow indicator 22. A housing 23 surrounds the flow indicator and defines a viewing window or port. The viewing port may be made translucent or transparent, such that the user may observe the movement of the flow indicator. Alternatively, the viewing window where the mechanical flow indicator 22 is located may be made opaque or obscured with a non-see through coating or color, such that the user is only able to observe the electronic indicator 220. In this latter embodiment, the user or caregiver would only see one indicator. Various respiratory care systems may include without limitation a valved holding chamber 2, a dry powder inhaler 4, a positive expiratory pressure device 6 or a nebulizer 8.

In one embodiment, shown in FIGS. 1-6, 10-19, and 50-53, a mechanical flow indicator 22 functions as an electrical switch as it moves between first and second positions during inhalation, for example as a flow path (P) is created along an inhalation path defined between the input and output ends 12, 14 of the holding chamber 2. An MDI includes a medicament canister 13 and an actuator boot 15, having a mouthpiece that is fitted within said input end 12, for example with a friction fit. In this embodiment, the mechanical flow indicator 22 may be positioned outside of the inhalation path (P), but is responsive to flow along the flow path, for example by way of a negative pressure being created. It should be understood that the flow indicator may also be configured to move during exhalation. Various aspects of the flow indicator are shown for example and without limitation in U.S. Pat. No. 8,550,067 for a "Visual Indicator for An Aerosol Medication Delivery Apparatus and System," the entire disclosure of which is hereby incorporated herein by reference.

As shown in FIGS. 1-4, 52 and 53, the valved holding chamber 2 includes a front piece, or patient interface 16, having an adapter 24 or baffle section, otherwise referred to as a retainer, releasably secured to the end of the valved holding chamber, for example with tabs. A mouthpiece section 26 is coupled to the baffle section, for example with tabs 28 engaging openings 30. As shown in FIGS. 22, 38-39, 52 and 53, the adapter or baffle section includes an annular attachment collar 32 with slots 34, a transition piece 36 and a cylindrical exit port 38. The adapter is attached to the chamber by snap inserting tabs 40 on the chamber housing into the slots 34 and then twisting the chamber housing or adapter so that the tabs are locked into place within the slots. The baffle section 24 may alternatively be integrally formed as an end portion of the holding chamber.

An inhalation valve 241 is seated on a front surface 42 of a baffle, which defines a valve seat. The inhalation valve is formed as an annular valve in one embodiment. The annular valve 241 has a central opening with an inner peripheral sealing edge 44 that seals against the valve seat 42. An outer peripheral edge 46 of the annular valve defines an exhalation valve that seats against a valve seat 48 defined by the mouthpiece. The inhalation valve may alternatively be formed as a duckbill valve, center post valve, slit petal valve and/or flap valve. The valve may be made of a soft plastic, such as silicone or a thermoplastic elastomer.

Figure 23:
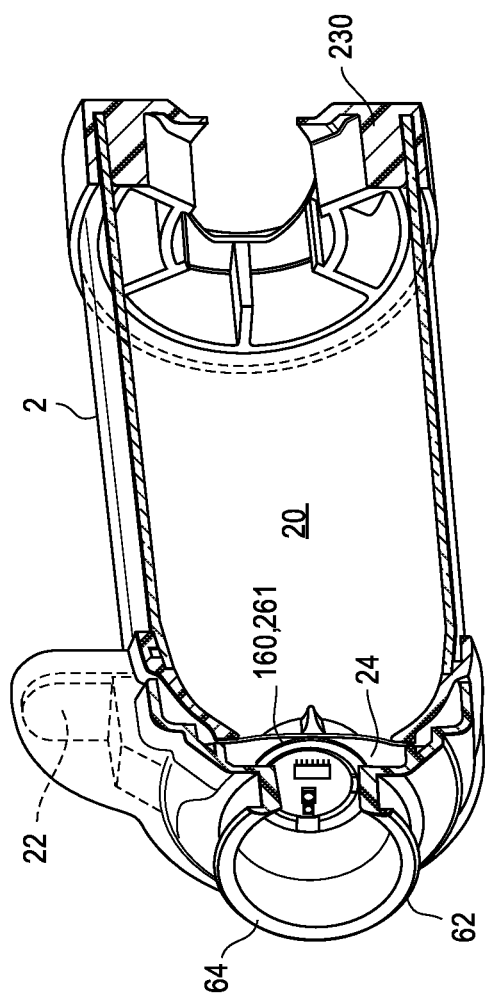
FIG. 23 is a cross-sectional view of a medicament delivery device incorporating the end assembly of FIG. 22.
Figure 24:
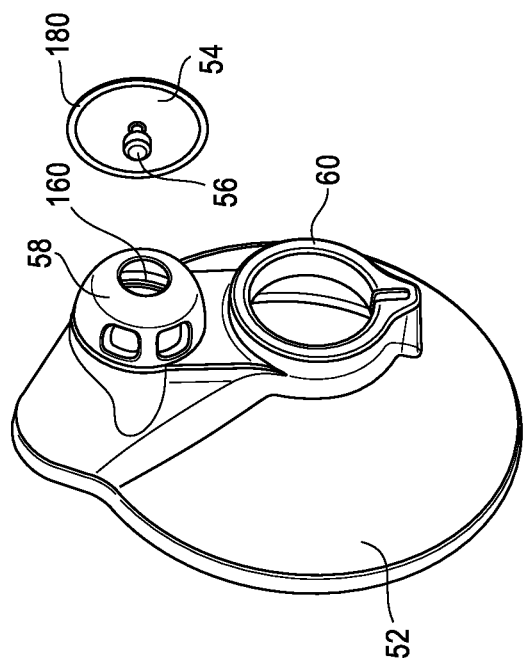
FIG. 24 is an exploded view of a mask assembly having a valve.
Figure 29:
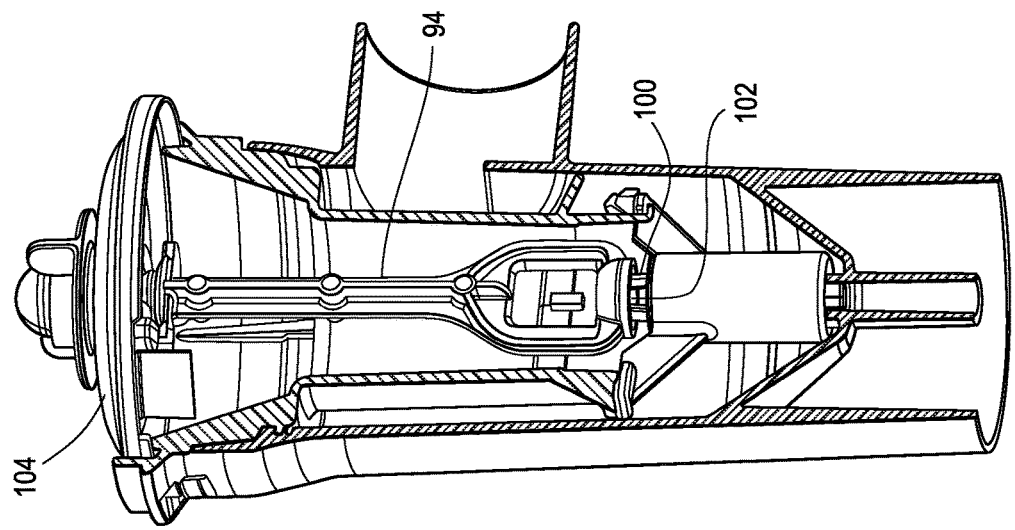
FIG. 29 is a cross-sectional view of the nebulizer shown in FIG. 28.
Figure 28:
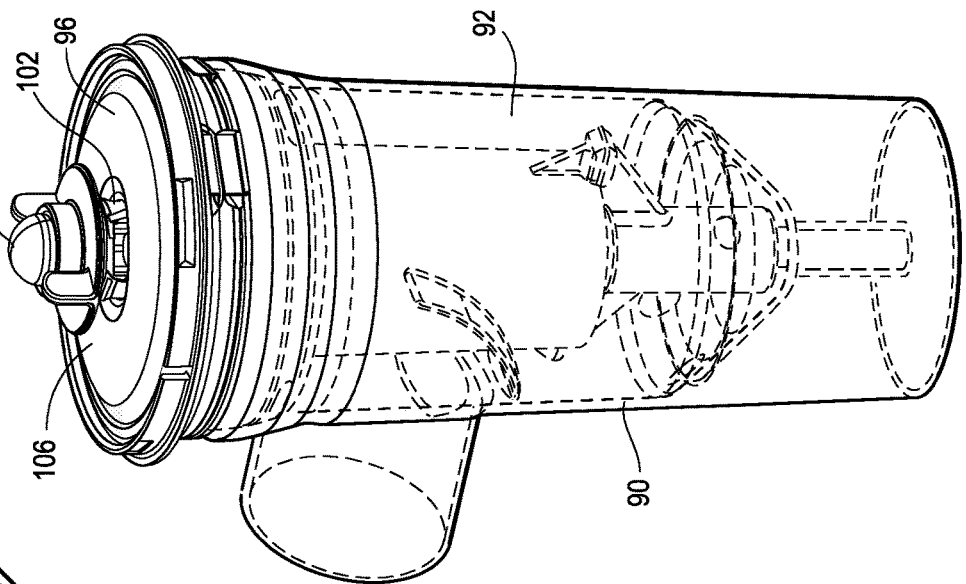
FIG. 28 is a perspective view of a nebulizer having a diaphragm.
Figure 27:
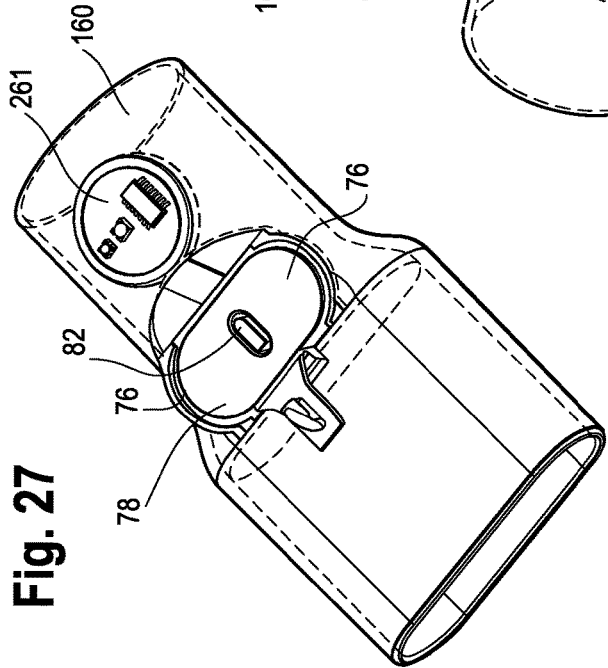
FIG. 27 is a perspective view of the mouthpiece of FIG. 26.
Figure 32:
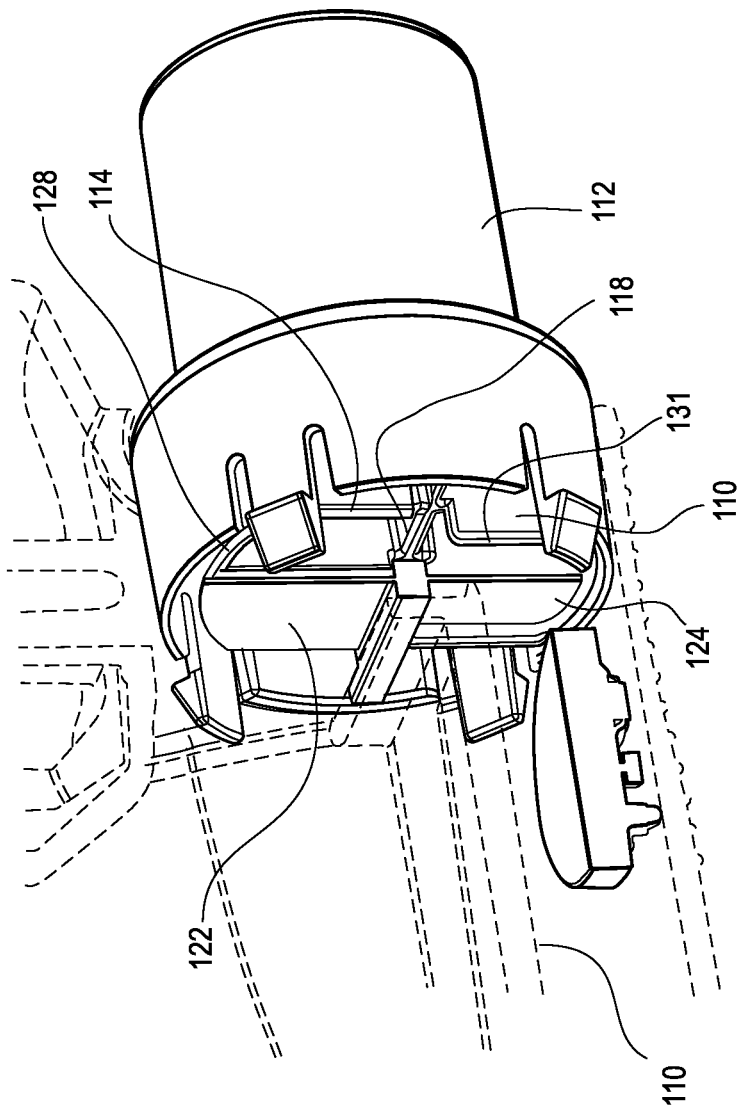
FIG. 32 is an enlarged, partial view of the device shown in FIG. 31.
Figure 51:
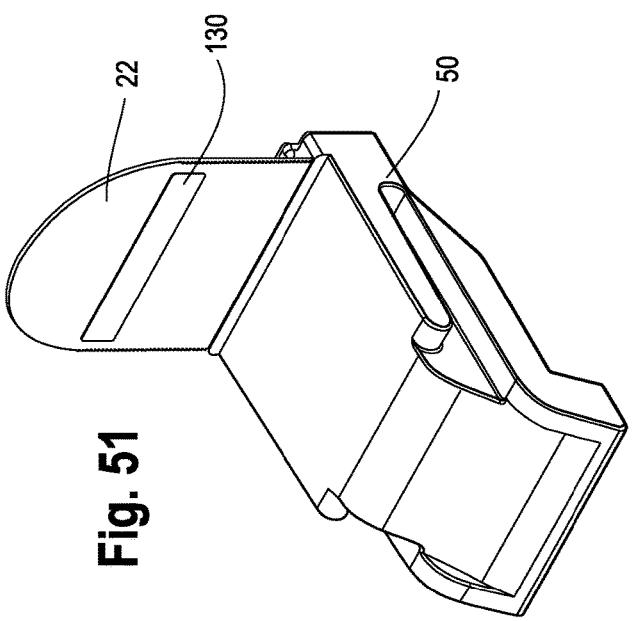
FIG. 51 is a perspective view of a flow indicator.

The flow indicator 22 may be integrally attached to the inhalation valve, or separately formed as shown in FIG. 51. In either embodiment, the flow indicator is hingedly connected to the valve or a base 50, for example with living hinge formed at the junction thereof, or with a hinge pin. The base 50 may be secured to the valved holding chamber or the user interface. The resiliency of the flow indictor biases the indicator to an at rest position. The flow indicator provides a visual indicator to the user or caregiver that the user is inhaling. The flow indicator may be rectangular in shape, although other shapes, such as a square or an ellipse, may also be suitable. For example, the visual flow indicator may have a rounded top edge as shown in FIGS. 23 and 51.

Referring to the embodiment of FIGS. 65 and 66A-C, the mechanical flow indicator 22 is positioned in a housing 23 located at the input end of holding chamber 2. The flow indicator may be incorporated into a backpiece 230, secured to the input end of the chamber. In this embodiment, the mechanical flow indicator 22 is configured to provide a range of electrical responses, rather than a simple normally open or closed switch. In on embodiment, the flow indicator 22 is configured with, or incorporates, a flexible resistor. As the flow indicator 22 is deformed (e.g., bent) greater amounts, as shown in FIGS. 66A-C, the resistance is varied, e.g., increased (or decreased). The resistor is incorporated into a circuit coupled to an electronic indicator, shown in this embodiment as an array of lights 1040, e.g., LED's, as further explained below. In this embodiment, the flow indicator is positioned outside the flow path P, but ambient air is entrained through an opening in the housing 23, whether formed as a part of the back piece 230 or as part of the holding chamber 2. The air flow past the indicator 22 causes the flow indicator bend a greater or lesser amount depending on the flow rate or volume. As a starting point, when the system is at rest, and the flow indicator is at rest, as shown in FIG. 66A, the resistance of the resistor in the circuit will cause a single light to illuminate, providing indicia that the system is ready, or there is no flow. As the patient inhales, the magnitude of the flow will rise to a predetermined desired flow rate, which causes the flow indicator 22 to bend, with the resistance being varied to signal the circuit to illuminate additional lights.

For example, a range of acceptable flow rates/volumes may be registered by the flow indicator bending between upper and lower limits, with the corresponding resistance change causing the circuit to illuminate between 2 and 3 additional lights for example. If the flow is too great, the flow indicator may bend beyond the acceptable range, causing an additional light (for example a different color, intensity or blinking) to illuminate and providing feedback that the flow rate is too great. This electronic indicator thereby provides feedback to the user and/or caregiver about the proper usage of the device. The array of lights may provide various indicia, such as change in colors (green to yellow to red) associated with acceptable, borderline and unacceptable flows. The circuit, which may include a microprocessor, or may communicate with a remote computer or processor as further explained below in connection with FIGS. 69 and 70, may also record the length or duration of the inhalation sequence, or the length or duration of the inhalation in the predetermined, acceptable flow range.

Figure 55:
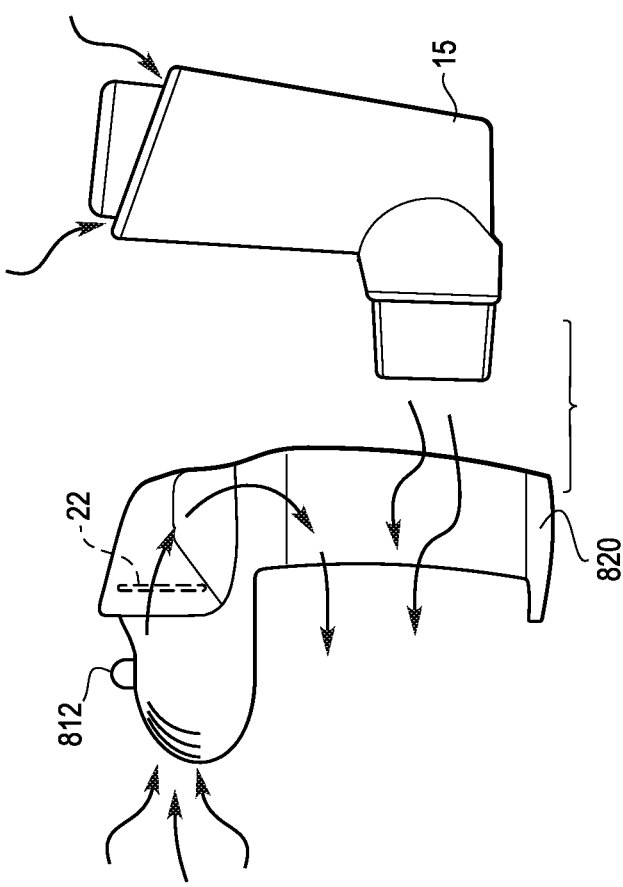
FIG. 55 is a side view of a metered dose inhaler being applied to another embodiment of a valved holding chamber.
Figure 56:
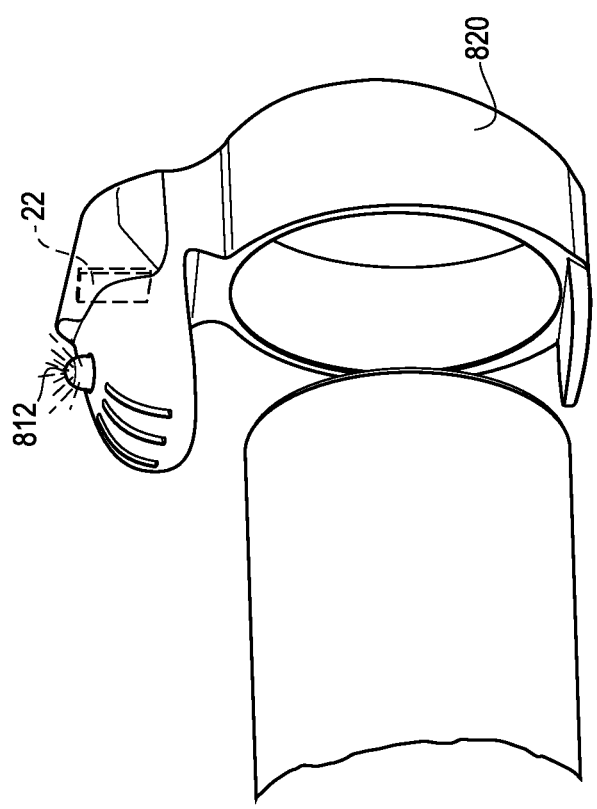
FIG. 56 is an enlarged exploded view of the valved holding chamber and end piece shown in FIG. 55.

Referring to the embodiment of FIGS. 55 and 56, and similarly to FIG. 65, the mechanical flow indicator 22 and electronic flow indicator 220 are housed at the input end of the valved holding chamber. In this embodiment, a back piece 820 is configured with a housing 23, which houses the flow indicator. Again, ambient air is drawn through openings in the housing, causing the flow indicator to deflect/deform/bend. The flow indicator may close a switch, or incorporate a resistor that changes resistance, so as to provide input to a circuit and a signal to the electronic indicator 220 that flow, for example by way of inhalation, is occurring. The flow indicator may be configured to deflect in either direction. The flow indicator and electronic indicator may also be incorporated into a whistle, for example a slot provided in the back piece. By locating the indicator at the input end of the chamber, the system is provided with a secondary flow path into the chamber, but avoids the possibility of leakage at the output end/user interface. In addition, the electronic indicator may be more visible to the user, due to the increased line of sight.

In one embodiment, shown in FIG. 68, a metered dose inhaler (MDI) includes actuator boot 15, medicament canister 13 and adapter 802. The adapter 802 has an input end 804 shaped to receive a mouthpiece portion 806 of the boot, and an output end 808 shaped to be received in an opening of the input end of the valved holding chamber, for example as formed in the back piece 230. As the canister 13 is discharged, aerosolized medicament is discharged through the mouthpiece 806 and adapter 802 and into the valved holding chamber 2. The adapter 802 may include a housing 23 and a flow indicator 22. The adapter may be configured with an upstanding flange, or standard/upright 810, which extends radially beyond an outer circumferential surface of the holding chamber such that an electronic indicator 812, such as a light, disposed on the upright is visible to the user of the holding chamber. It should be understood that the adapter may be used without a holding chamber, with the output end 808 configured and serving as a mouthpiece that may be inserted into the mouth of a user. The flow indicator 22, circuitry and electronic indictor 812 function as described herein elsewhere with respect to other embodiments. Because the electronic components are incorporated into the back piece in this embodiment, the back piece may be removed for cleaning, for example high temperature cleaning like dishwashing and/or autoclaving, which avoids the need to insulate the components from heat and/or water, e.g., water proofing. This in turn allows for the components to be manufactured with less expense.

Figure 57:
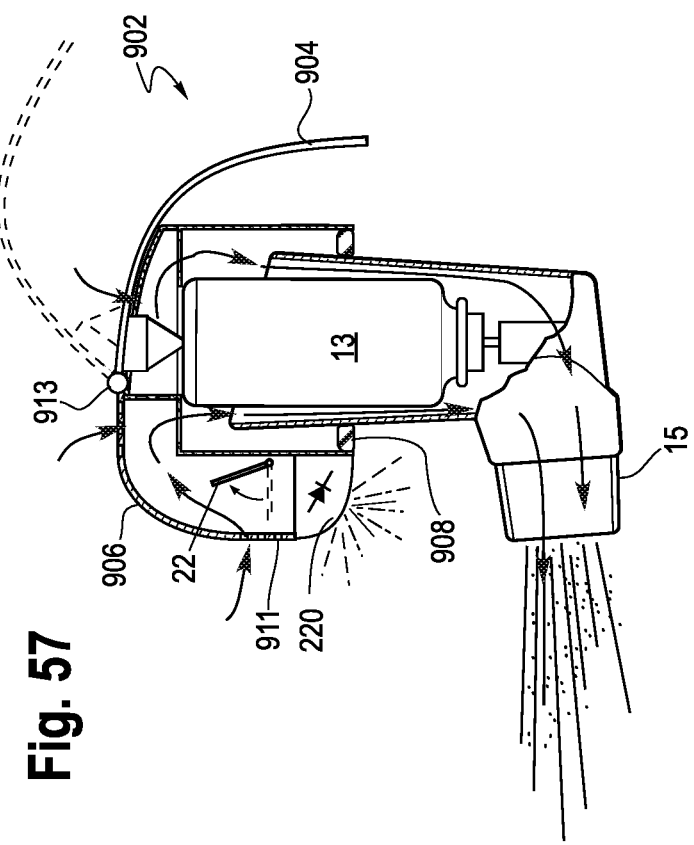
FIG. 57 is a schematic cross section of a metered dose inhaler actuation assist device.

Now Referring to FIG. 57, one embodiment of a MDI positioned in a MDI applicator 902 is shown. The MDI applicator 902 may include a lever 904 and a housing 906. The constructions of various embodiments of an applicator are disclosed in U.S. Pub. No. 2014/0318534A1, filed Mar. 14, 2014, published Oct. 30, 2014, and entitled "Metered Dose Inhaler Applicator," the entire disclosure of which is hereby incorporated herein by reference. The components may be made of various material, including for example plastics used in the injection molding industry, for example polypropylene, ABS and acetal. The lever 904, which is moveably coupled to the housing 906, for example by way of a pivoting about a pivot axis/axle or hinge, assists the user, whether a patient or caregiver, in actuating a MDI. The housing is coupled to the MDI, for example with a stretchable seal 908. A flow indicator 22 is positioned in the housing 906, with an electronic indicator 220 disposed in the housing and visible to the user. The electronic circuitry is further disposed in the housing. Air flow may be entrained through various openings 911, 913 in the housing, for example in the top of the housing above the canister, or along the side of the housing as shown in FIG. 57, causing the flow indicator 22 to move, with an associated signal being sent to the electronic indicator.

Figure 72:
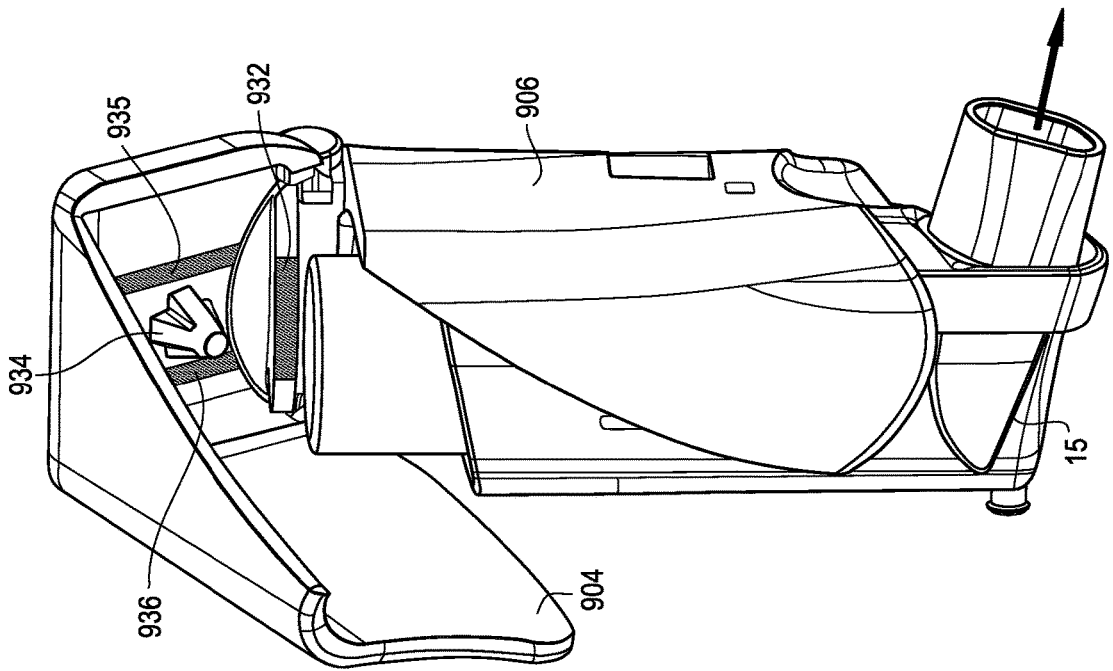
FIG. 72 is a front view of the embodiment of the MDI shown in FIG. 5 with the MDI positioned in an actuated position in a MDI applicator.
Figure 71:
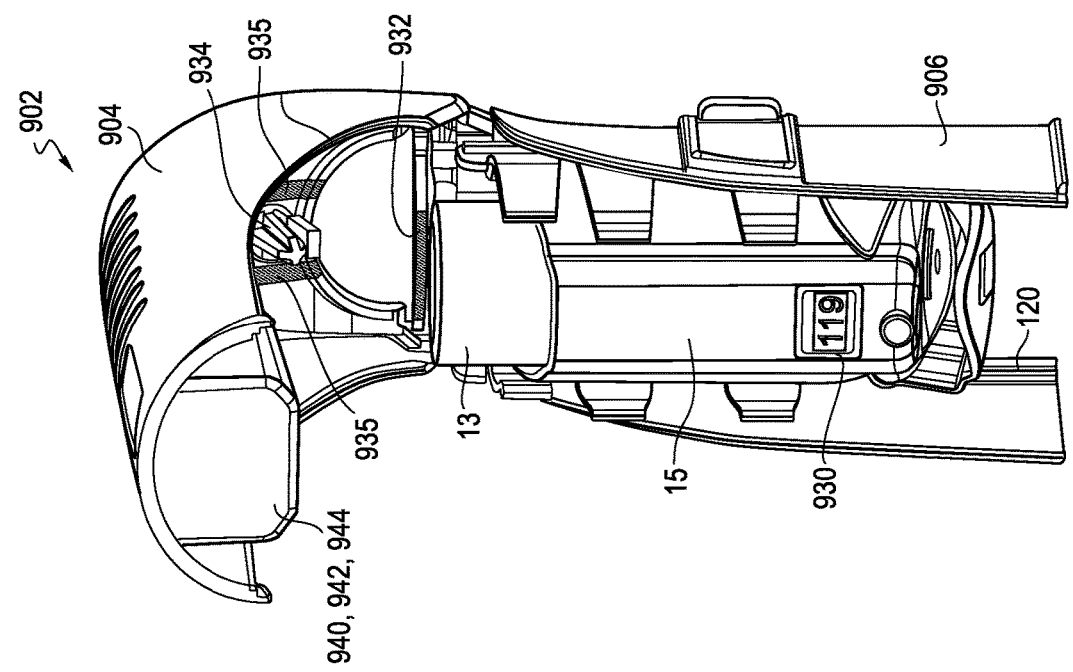
FIG. 71 is a rear view of the MDI positioned in the MDI applicator of FIGS. 1 and 2 with the lever in a raised position.
Figure 73:
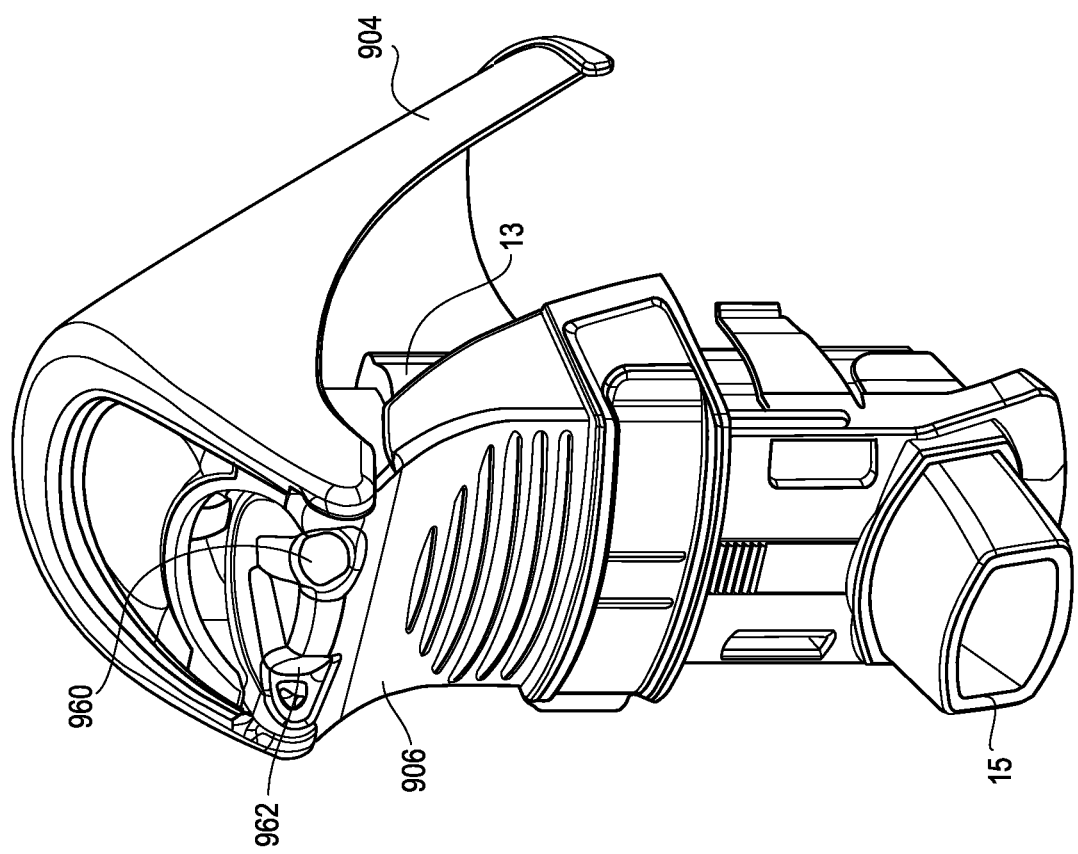
FIG. 73 is a perspective view of another embodiment of a MDI positioned in an MDI applicator.

Referring to FIGS. 71-73, the MDI boot 15 may be positioned into the applicator 902. The lever 904 is then rotated or pivoted relative to the housing about a pivot axis to an at-rest position, with a post 934 of the lever 904 positioned against an end of the canister 13 of the MDI. A force may be applied to the lever 904 of the MDI applicator 902, which lever 904 pivots about the pivot axis relative to the housing and MDI. The pivotal movement of the lever 904 and the post 934 transfers the force applied to the lever 904 to a downward force against the canister 13 of the MDI. When the downward force against the canister 13 of the MDI causes a stem of the MDI to compress enough to open an internal valve of the MDI, medicine within the canister passes through the stem and out of a nozzle of the MDI in an aerosolized form for inhalation by a patient. The pivot axis is oriented substantially orthogonal to the mouthpiece, or an axis defined by the flow path exiting therefrom. When sufficient force is applied to the canister 13 of the MDI via the lever 904, the MDI dispenses an aerosolized medicine, for example through a mouthpiece, or into a valved holding chamber 2, which may thereafter be inhaled by a patient.

Specifically, as the lever 904 is depressed, the canister 13 of the MDI is forced into the actuator boot 15, which has a well receiving the valve stem in one embodiment. Once the canister has travelled far enough into the boot 15, the valve stem is depressed by the well until the valve is opened, thereby releasing the dose of aerosolized medicine. The MDI may be configured with a dose counter 930, for example a mechanical or electronic dose counter, which records the number of actuations of the canister.

Referring to the embodiment shown in FIGS. 82, the lever is pivotally coupled to the housing about an axis, which is oriented parallel to the flow path axis, or forms an acute angle relative thereto. This alternate lever position provides improved comfort to at least some users.

The movement of the lever 904 relative to the housing 906, canister 13 or boot 15, provides input to an electronic actuation indicator/tracker that signals and/or records that an actuation of the canister has occurred. For example, in the embodiments shown in FIGS. 71 and 72, a conductive portion, e.g., strip 935, is disposed on a surface of the lever and leads to a microcontroller 940, which may be housed in a case 942. The lever further includes a conductive portion, e.g., strip 936, that leads to a battery 944, which may also be housed in the case 942. A conductive portion, e.g., strip 932, is disposed on the housing 906, or alternatively on the canister or boot. It should be understood that the lever and housing may include other electrically conductive properties, or be integrally formed from a conductive material, isolated at attachment points by an insulator, or include various conductive portions, whether applied as a separate member or integrally formed. The case 942 may be disposed in and coupled to the lever 904. It should be understood that the strips 935, 936 and case 942, with battery 944 and controller 940, may be disposed on or coupled to the housing 906, boot 15 or canister 13, with strip 932 disposed on the lever. The strips 932, 935, 936 act as a (normally open) switch when the lever is a raised and/or at-rest position as shown in FIGS. 71 and 72. As the lever is pivoted to an actuation position, the strip 932 is brought into contact with and electrically connects strips 935, 936, with the strips 932, 935, 936 functioning as a closed switch. The completion of the circuit 936, 932, 935 signals the microcontroller to record an actuation of the MDI and acquire a time stamp associated with the actuation and store the data on the onboard memory, or communicate the data to a remote server or local computing device as further explained below. The switch is closed (or opened) when the lever has been displaced a predetermined minimum distance. The switch may alternatively be configured as a limit switch, wherein the switch is activated only when the lever has travelled a certain distance, or pivoted through a certain angle. The switch may be toggled by contacting the housing, MDI canister and/or actuator.

The applicator may also be configured with an electronic indicator, such as an LED disposed on one of the lever or housing, which provides indicia that an actuation has occurred. The activation of the circuit by the closing of the switch may activate the electronic circuit utilizing low power circuitry enclosed within a portion of the lever or housing, for example the controller. The conductive properties may be specific to a small region of the lever and housing, e.g., a thin strip or other geometry, or the entire end of the housing may be conductive. Alternatively, the system uses capacitive sensing to determine when the lever has reached an actuation position. Feedback from the electronic indicator indicates that a sufficient actuation is achieved.

In other embodiments, the switch may be a normally closed switch, which activates the circuit when the switch is opened, for example when the lever is pivoted. Actuation may also be detected by a pressure sensor, a capacitive sensor, an inductive sensor, or other proximity sensor or switch. Upon reaching a predetermined second position, the electrically conductive properties of the lever and/or housing act as a switch, whether open or closed, to activate the electronic feedback utilizing low power circuitry enclosed with the housing 942, located on the lever, housing or MDI. The switch on the mating surface may be configured as two small conductive point contacts or conductive pads, emerging from an encapsulated, potted, conformal coated or sealed printed circuit board (PCB). If the switch is created using capacitive sensing, the sensor within the encapsulation is a small pad and a ground pad matching the size of the PCB at a minimum to increase sensitivity of the sensor. The ground pad may be incorporated within the encapsulation or may be formed by a conductive path from the conductive region of the indicator along one of the applicator or MDI components. The human body may come in contact with the conductive path while holding the applicator and act as a ground.

The electronic components may be integrated in the assembly of the device or embodied in a modular component or housing 942 that can be fit to any MDI or applicator. In either scenario, the electronic components are encapsulated, potted, conformal coated or sealed in the housing 942. It should be understood that in the various embodiments, the circuitry is not visible to the user or caregiver.

Referring to the alternative embodiment of FIG. 73, the housing 906 is configured with an IR detector 962 and emitter 960. Then the canister is in the at-rest position, infrared radiation is emitted from the emitter 960 along a radiation path, reflected off of the canister 13 along a radiation path, and detected by the detector 62. When the MDI is actuated, the canister moves downwardly in response to the force from the lever 904 until the canister is no longer in the radiation path. In other words, in the actuated position, the canister 13 is no longer in a position to reflect the infrared radiation path, and the change of signal from the detector 962 is used to infer actuation.

In another embodiment, the emitter 960 and detector 962 may be positioned 180 degrees apart from one another, with the canister 13 breaking the radiation beam there between. In this embodiment, when the lever and canister are in the at-rest position, no radiation emitted from the emitter 960 is detected by the detector 962. During actuation, the canister moves out the path, such that the detector 962 detects the radiation beam from the emitter 960, and thereby senses and sends a signal associated with an actuation of the MDI. Light curtain and reflection/proximity sensing embodiments and configurations may also be suitable.

Referring to an alternative embodiment, a force sensor is provided on the lever. The force sensor may serve the function of the post 934, or be incorporated into the post. Actuation of the MDI occurs at a fairly consistent force. Accordingly, the force sensor may be correlated with the actuation force, and send a signal when the lever is pivoted to apply such a force. For example, once a certain threshold value is recorded or detected by the sensor, an actuation is recorded/registered. The microcontroller, battery and case may be incorporated into the lever as disclosed above. Alternatively, the force sensor may be applied to the housing 906 or MDI, and electronically communicate with the electronic components associated therewith.

It should be understood that the different modules and embodiments may record and register actuations, individually and cumulatively, including the time and date of the actuation, and/or the location when the device is configured and/or associated with a GPS module, which may be embedded in, or housed with, the microcontroller. The accumulated data may be analyzed to provide feedback on when and how the device is used, and/or compliance with particular delivery protocols prescribed by the caregiver.

In order to provide faster and more accurate processing of the sensor data generated within the MDI applicator, data may be wirelessly communicated to a smart phone, local computing device and/or remote computing device to interpret and act on the raw sensor data.

Figure 64:
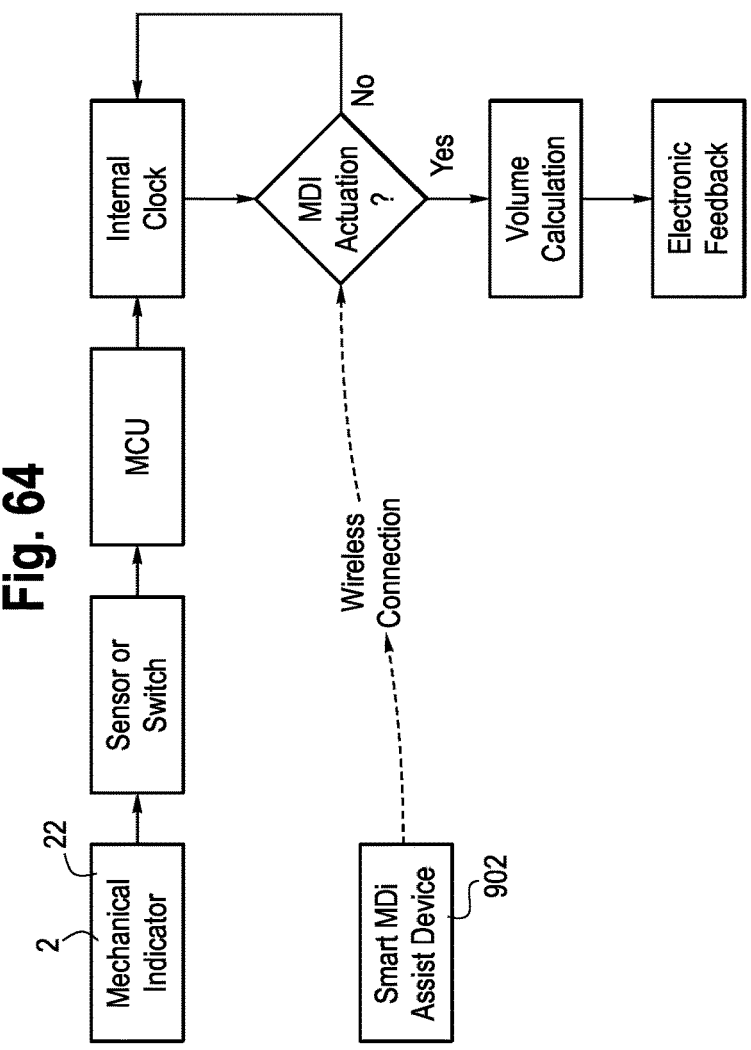
FIG. 64 is a schematic flow chart illustrating the operation of a metered dose inhaler actuation assist device and valved holding chamber.

Referring to FIG. 64, the MDI applicator 902, for example as disclosed in FIGS. 71-73, may be used with a holding chamber (e.g., FIGS. 1-5), which is configured with a flow indicator. The MDI applicator 902 may be configured with a module as disclosed above that records and registers actuations, individually and cumulatively, including the time and date of the actuation, and/or the location when the device is configured and/or associated with a GPS module, which may be embedded in, or housed with, a microcontroller disposed on or in the housing. The accumulated data may be analyzed to provide feedback on when and how the device is used, and/or compliance with particular delivery protocols prescribed by the caregiver.

In order to provide faster and more accurate processing of the sensor data generated within the MDI applicator, or the other devices (e.g., holding chamber, peak flow meters, dry powder inhalers, nebulizers, etc.) disclosed herein, data may be wirelessly communicated to a smart phone, local computing device and/or remote computing device to interpret and act on the raw sensor data.

Figure 69:
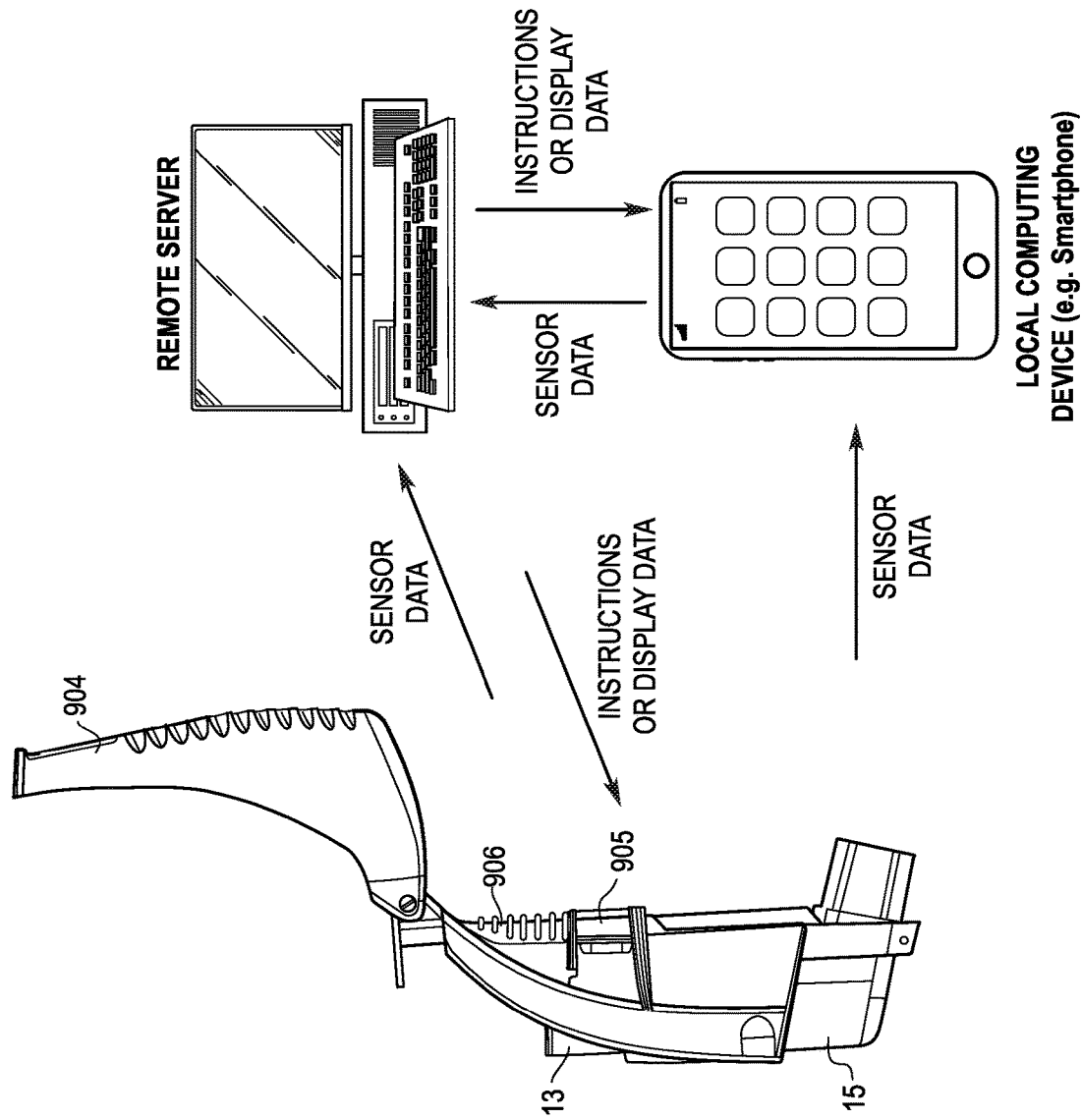
FIG. 69 is a schematic showing a system with communication between the MDI applicator and remote server and/or local computing device.
Figure 70:
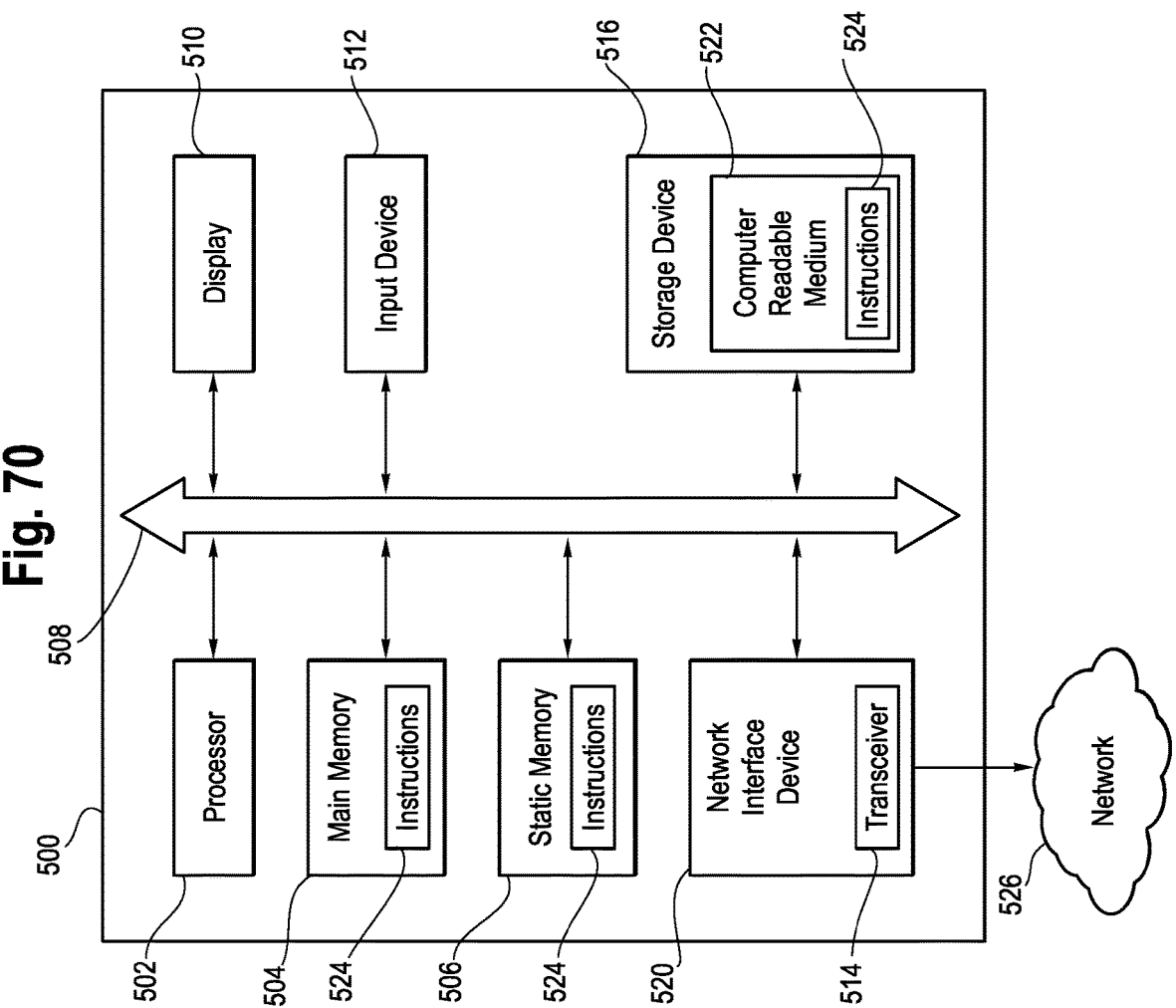
FIG. 70 is a schematic showing the computer and network used in the system of FIG. 69.

Referring to FIGS. 64, 69 and 70, the MDI applicator 902, or other device (e.g., holding chamber, peak flow meters, dry powder inhalers, nebulizers, etc.), includes circuitry for transmitting raw sensor data in real time to a local device, such as a smart phone. The smart phone may display graphics or instructions to the user and implement processing software to interpret and act on the raw data. The smart phone may include software that filters and processes the raw sensor data and outputs the relevant status information contained in the raw sensor data to a display on the smart phone. The smart phone or other local computing device may alternatively use its local resources to contact a remote database or server to retrieve processing instructions or to forward the raw sensor data for remote processing and interpretation, and to receive the processed and interpreted sensor data back from the remote server for display to the user or a caregiver that is with the user of the smart MDI applicator.

In addition to simply presenting data, statistics or instructions on a display of the smart phone or other local computer in proximity of the MDI applicator or other device (e.g., holding chamber, peak flow meters, dry powder inhalers, nebulizers, etc.), proactive operations relating to the MDI applicator may be actively managed and controlled. For example, if the smart phone or other local computer in proximity to the MDI applicator, or other device (e.g., holding chamber, peak flow meters, dry powder inhalers, nebulizers, etc.), determines that the sensor data indicates that a dose has been administered, the smart phone or other local computing device may communicate that information to the user or caregiver.

In yet other implementations, real-time data gathered in the smart MDI applicator or other device (e.g., holding chamber, peak flow meters, dry powder inhalers, nebulizers, etc.) and relayed via to the smart phone to the remote server may trigger the remote server to track down and notify a physician or supervising caregiver regarding a problem with the particular session or a pattern that has developed over time based on past sessions for the particular user. Based on data from the one or more sensors in the smart MDI applicator or other device (e.g., holding chamber, peak flow meters, dry powder inhalers, nebulizers, etc.), the remote server may generate alerts to send via text, email or other electronic communication medium to the user's physician or other caregiver. The data may be uploaded to a mobile application via wireless communications (e.g., Bluetooth) whenever the mobile device (e.g., phone, tablet, laptop, etc.) is in range for synchronizing the data. The data my then be analyzed on the application and presented to the user in a manner that is beneficial for the user/patient's engagement and adherence/compliance. The data may also be forwarded to a cloud service via WiFi or mobile network so that the data may be reviewed by other caregivers, healthcare providers and/or payers (e.g., insurance companies).

Figure 7:
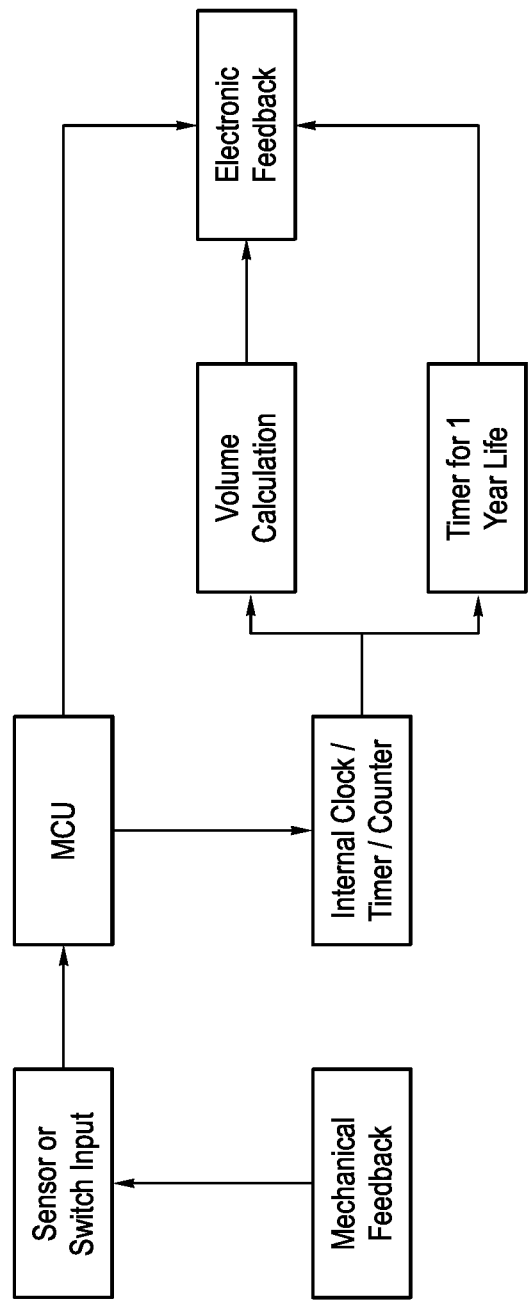
FIG. 7 is a schematic flow chart diagram showing the operation of the electronic indicator.

By combining the applicator 902 and valved holding chamber configured with an electronic indicator 220, a more accurate calculation of the end of treatment may be provided to the user or care giver. For example as shown in FIGS. 7 and 64, the applicator 902, or microcontroller 940, registers an actuation of the MDI and communicates that information, or sends a signal, to a processor, for example by wireless communication. In other embodiments the applicator and valved holding chamber may communicate by direct communication links, for example hard wiring when the applicator is inserted into the valved holding chamber. In operation, the mechanical flow indicator 22 provides input, or sends a signal, that inhalation has commenced by closing a switch, or actuating another sensor, as disclosed above. That information is communicated to a microcontroller (MCU) or microprocessor. An internal clock records the time, while the processor identifies whether the MDI actuation has taken place by way of communication of the signal from the applicator 902. If the actuation has not transpired, the internal clock loops, and/or computes the time from actuation, such that data is gathered as to the length of the inhalation through the valved holding chamber, which causes the flow indicator associated therewith to move or deform and send a signal, as well as the length of the inhalation after the MDI is actuated. Once an MDI actuation has occurred, as recorded by the applicator 902 and controller 940, a volume calculation is performed, using the data as to the inhalation flow before and after actuation, with electronic feedback provided. In this way, feedback is provided that treatment is finished, or that sufficient volume has been inhaled subsequent to the actuation of the MDI. The data may also be collected and communicated as noted to the healthcare provider.

The electronic circuitry in the MDI applicator or other device (e.g., holding chamber, peak flow meters, dry powder inhalers, nebulizers, etc.) may include some or all of the capabilities of a computer 500 in communication with a network 526 and/or directly with other computers. As illustrated in FIGS. 69 and 70, the computer 500 may include a processor 502, a storage device 516, a display or other output device 510, an input device 512, and a network interface device 520, all connected via a bus 508. The computer may communicate with the network. The processor 502 represents a central processing unit of any type of architecture, such as a CISC (Complex Instruction Set Computing), RISC (Reduced Instruction Set Computing), VLIW (Very Long Instruction Word), or a hybrid architecture, although any appropriate processor may be used. The processor 502 executes instructions and includes that portion of the computer 500 that controls the operation of the entire computer. Although not depicted in FIG. 70, the processor 502 typically includes a control unit that organizes data and program storage in memory and transfers data and other information between the various parts of the computer 500. The processor 502 receives input data from the input device 512 and the network 526 reads and stores instructions (for example processor executable code) 524 and data in the main memory 504, such as random access memory (RAM), static memory 506, such as read only memory (ROM), and the storage device 516. The processor 502 may present data to a user via the output device 510.

Although the computer 500 is shown to contain only a single processor 502 and a single bus 508, the disclosed embodiment applies equally to computers that may have multiple processors and to computers that may have multiple busses with some or all performing different functions in different ways.

The storage device 516 represents one or more mechanisms for storing data. For example, the storage device 516 may include a computer readable medium 522 such as read-only memory (ROM), RAM, non-volatile storage media, optical storage media, flash memory devices, and/or other machine-readable media. In other embodiments, any appropriate type of storage device may be used. Although only one storage device 516 is shown, multiple storage devices and multiple types of storage devices may be present. Further, although the computer 500 is drawn to contain the storage device 516, it may be distributed across other computers, for example on a server.

The storage device 516 may include a controller (not shown) and a computer readable medium 522 having instructions 524 capable of being executed on the processor 502 to carry out the functions described above with reference to processing sensor data, displaying the sensor data or instructions based on the sensor data, controlling aspects of the smart MDI applicator or other device (e.g., holding chamber, peak flow meters, dry powder inhalers, nebulizers, etc.) to alter its operation, or contacting third parties or other remotely located resources to provide update information to, or retrieve data from those remotely located resources. In another embodiment, some or all of the functions are carried out via hardware in lieu of a processor-based system. In one embodiment, the controller is a web browser, but in other embodiments the controller may be a database system, a file system, an electronic mail system, a media manager, an image manager, or may include any other functions capable of accessing data items. The storage device 516 may also contain additional software and data (not shown), which is not necessary to understand the invention.

The output device 510 is that part of the computer 500 that displays output to the user. The output device 510 may be a liquid crystal display (LCD) well-known in the art of computer hardware. In other embodiments, the output device 510 may be replaced with a gas or plasma-based flat-panel display or a traditional cathode-ray tube (CRT) display. In still other embodiments, any appropriate display device may be used. Although only one output device 510 is shown, in other embodiments any number of output devices of different types, or of the same type, may be present. In an embodiment, the output device 510 displays a user interface. The input device 512 may be a keyboard, mouse or other pointing device, trackball, touchpad, touch screen, keypad, microphone, voice recognition device, or any other appropriate mechanism for the user to input data to the computer 500 and manipulate the user interface previously discussed. Although only one input device 512 is shown, in another embodiment any number and type of input devices may be present.

The network interface device 520 provides connectivity from the computer 500 to the network 526 through any suitable communications protocol. The network interface device 520 sends and receives data items from the network 526 via a wireless or wired transceiver 514. The transceiver 514 may be a cellular frequency, radio frequency (RF), infrared (IR) or any of a number of known wireless or wired transmission systems capable of communicating with a network 526 or other smart devices 102 having some or all of the features of the example computer of FIG. 2. The bus 508 may represent one or more busses, e.g., USB, PCI, ISA (Industry Standard Architecture), X-Bus, EISA (Extended Industry Standard Architecture), or any other appropriate bus and/or bridge (also called a bus controller).

The computer 500 may be implemented using any suitable hardware and/or software, such as a personal computer or other electronic computing device. The computer 500 may be a portable computer, laptop, tablet or notebook computers, smart phones, PDAs, pocket computers, appliances, telephones, and mainframe computers are examples of other possible configurations of the computer 500. The network 526 may be any suitable network and may support any appropriate protocol suitable for communication to the computer 500. In an embodiment, the network 526 may support wireless communications. In another embodiment, the network 526 may support hard-wired communications, such as a telephone line or cable. In another embodiment, the network 526 may support the Ethernet IEEE (Institute of Electrical and Electronics Engineers) 802.3×specification. In another embodiment, the network 526 may be the Internet and may support IP (Internet Protocol). In another embodiment, the network 526 may be a LAN or a WAN. In another embodiment, the network 526 may be a hotspot service provider network. In another embodiment, the network 526 may be an intranet. In another embodiment, the network 526 may be a GPRS (General Packet Radio Service) network. In another embodiment, the network 526 may be any appropriate cellular data network or cell-based radio network technology. In another embodiment, the network 526 may be an IEEE 802.11 wireless network. In still another embodiment, the network 526 may be any suitable network or combination of networks. Although one network 526 is shown, in other embodiments any number of networks (of the same or different types) may be present.

It should be understood that the various techniques described herein may be implemented in connection with hardware or software or, where appropriate, with a combination of both. Thus, the methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or use the processes described in connection with the presently disclosed subject matter, e.g., through the use of an API, reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations. Although exemplary embodiments may refer to using aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be spread across a plurality of devices. Such devices might include personal computers, network servers, and handheld devices, for example.

Referring to FIGS. 58A and B, adapters 1000, 1002 for use in a ventilator circuit are shown, with the adapters inserted into a flow path between the ventilator and a user interface. The construction of the adapters is disclosed in U.S. Pub. No. 2014/0360498, filed Mar. 14, 2014, published Dec. 11, 2014, and entitled "Ventilator Circuit, Adapter for Use in Ventilator Circuit and Methods for The Use Thereof," the entire disclosure of which is hereby incorporated herein by reference. The adapters 1000, 1002 include medication delivery ports 1004, 1006, which are suited and configured to receive medicament delivery devices, including for example and without limitation inhalers 1008 and nebulizers 1010. The adapters 1000, 1002 are configured with a mechanical flow indicator 22 disposed in the flow path. The adapter may be configured with an electronic indicator 220, such as a light, disposed on an exterior surface of the adapter such that the indicator is visible to the user or care giver. The flow indicator 22, circuitry and electronic indictor 220 function as described herein with respect to other embodiments.

In a ventilator circuit, drug delivery is preferably performed at the onset of an inhalation cycle, which may be difficult for a care giver to ascertain by just listening to the ventilator machine. The indicator 220 provides more certainty, and helps prevent drug delivery from being performed during exhalation. In operation, the drug delivery devices 1008, 1010 are actuated when the mechanical indicator 22, which may be visible to the user, moves and/or when the electronic indicator 220 provides indicia, e.g., by illuminating. The indicator 22 may be made of silicone, and may operate as a switch (normally open or closed), or be configured with a flexible resistor in a circuit, as described herein elsewhere. As shown, the indicators 22 are positioned on the upper side of the adapter, or extend downwardly therefrom, when such adapters are in their normal use positions to prevent drug pooling or accumulation against the indicator 22.

Figure 59:
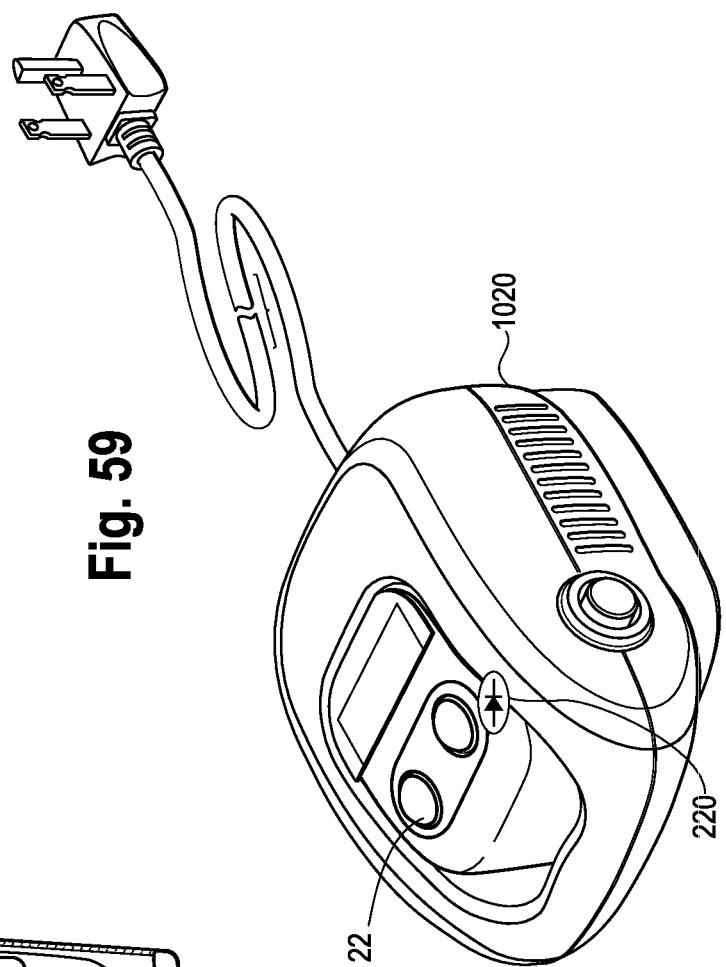
FIG. 59 is a perspective view of a compressor for use with a medication delivery system.

Referring to FIGS. 59 and 60, a compressor 1020, or tubing 1022 connecting the compressor or other air supply, may be configured with a mechanical flow indicator, which moves or is deformed in response to a fluid flow (P), whether gas or liquid. The flow indicator 22 is coupled to a circuit, which provides a signal to an electronic indicator 220 when actuated. The electronic indicator provides indicia to the user that flow is occurring. As shown in FIG. 59, the flow indicator 22 is embedded in a flow path in the compressor 1020, while an electronic indicator 220 is provided on or in the compressor, and is visible to the user if embodied as a visual indicator.

As shown in FIG. 60, the flow indicator may be positioned in a connector, or adapter, having an insert portion received in an end portion 1026 of the tubing 1022 and a receiving end connector portion 1028, which is shaped and configured to connect to the same devices as the end portion 1026 of the tubing. The flow indicator may alternatively be directly positioned in the tubing 1022 and operably connected to an electronic indicator, whether by direct circuitry or wirelessly.

Referring to FIG. 61, a peak flow meter 1050 is configured with a mechanical flow indicator 22, for example a flow indicator configured with a flexible resistor. The amount of flow deflects the indicator and deforms or bends the resistor varying amounts. The amount of deflection or deformation may be correlated with a varying display by an electronic indicator, for example an array of LED's 1040, with a greater number of LED's being illuminated as the flow increases. The indicator 1040 may also be configured with different color lights providing indicia about different flow levels. Usage data may also be collected and tracked, and connected to a computer or smartphone app, as described above with respect to the MDI applicator, such that the data may be shared with the patient, care giver or other healthcare providers.

In one embodiment, shown in FIGS. 24, 25 and 40-41A, the patient interface includes a mask 52 secured to an adapter 62, which in turn may be secured to the end of the valved holding chamber or the baffle section. The mask includes an exhalation valve 54, which functions as a flow indicator. Other patient interfaces may include for example and without limitation, various mouthpieces, masks, endotracheal tubes, etc. The valve may have a central post 56, which engages an opening on the mask and secures the valve to the mask. A protective dome or shroud 58 may be disposed around the valve. The exhalation valve 54 is inserted into an exit port formed in a nasal reception area of a mask and is attached thereto. Examples of various mask and exhalation valve embodiments are disclosed in U.S. Pat. Nos. 5,988,160 and 5,645,049, the entire disclosures of which are hereby incorporated herein by reference. A cylindrical input port 60 of the mask is placed over the exit port of the adapter and attached thereto by a friction fit, or by way of an interface of a rib 64 formed on the input port engaging a channel or corresponding rib on the mask 52.

Figure 8:
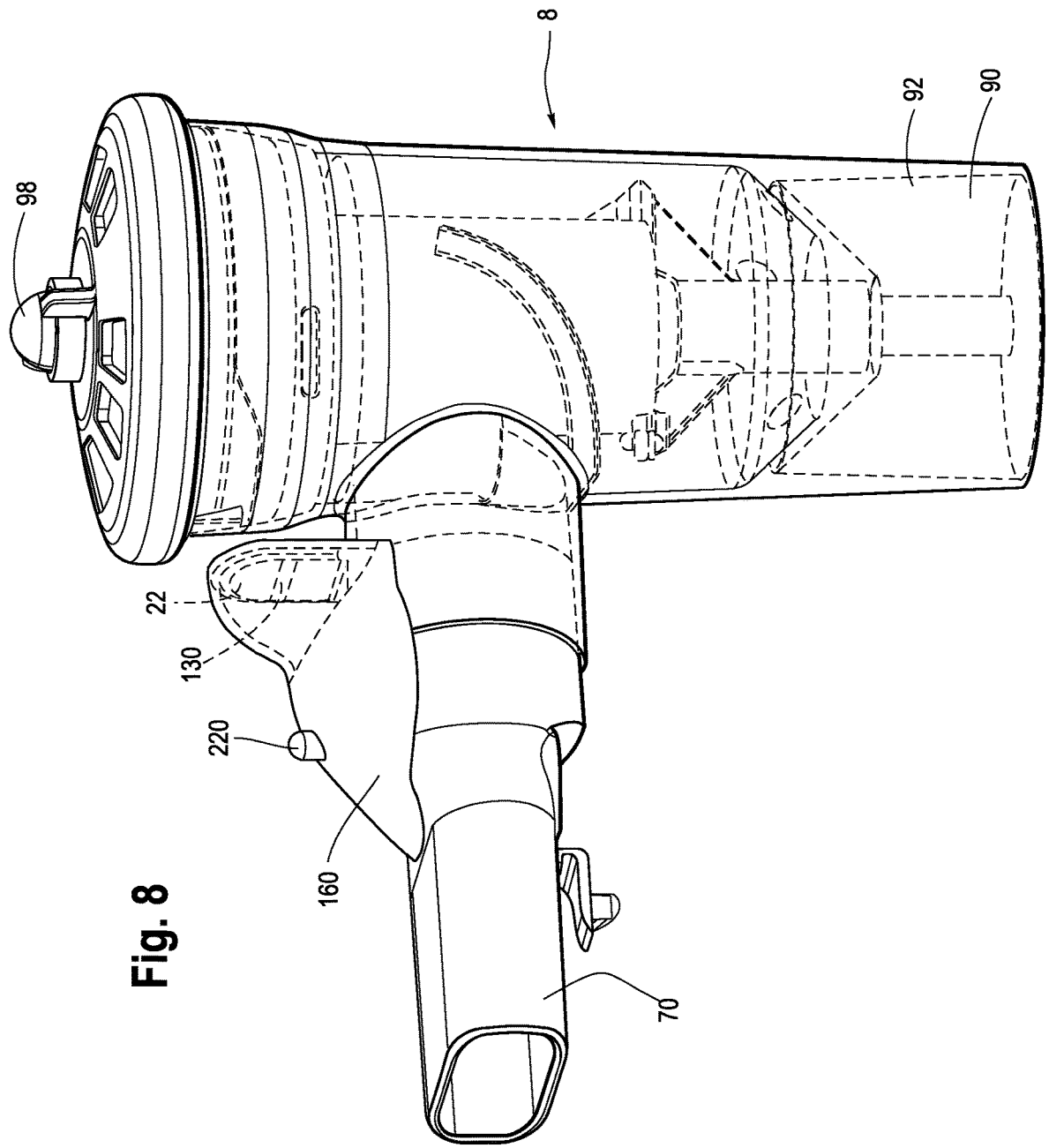
FIG. 8 is a perspective view of an embodiment of a nebulizer having a flow indicator and an electronic indicator.
Figure 9:
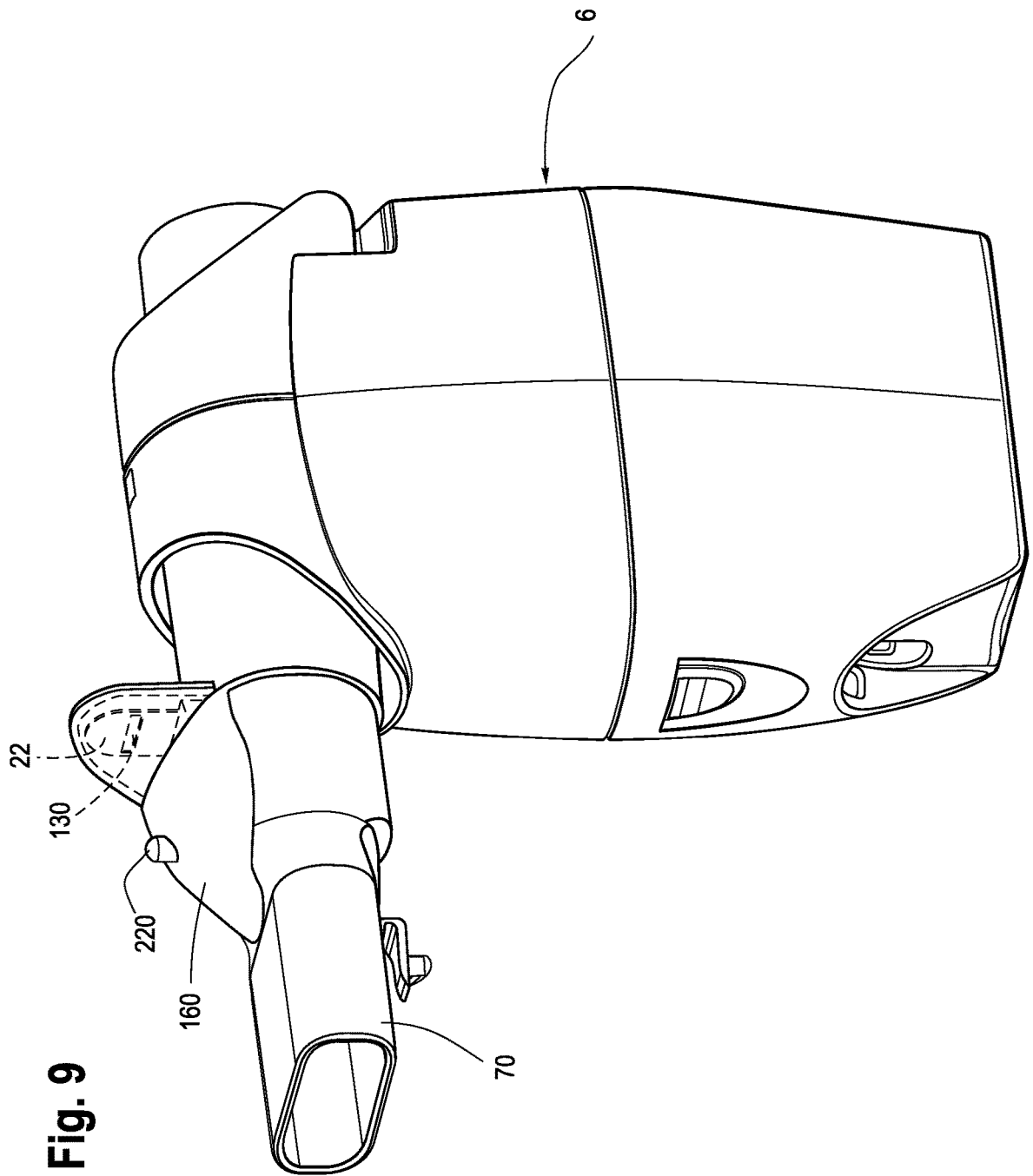
FIG. 9 is a perspective view of an embodiment of a positive expiratory pressure device having a flow indicator and an electronic indicator.
Figure 10:
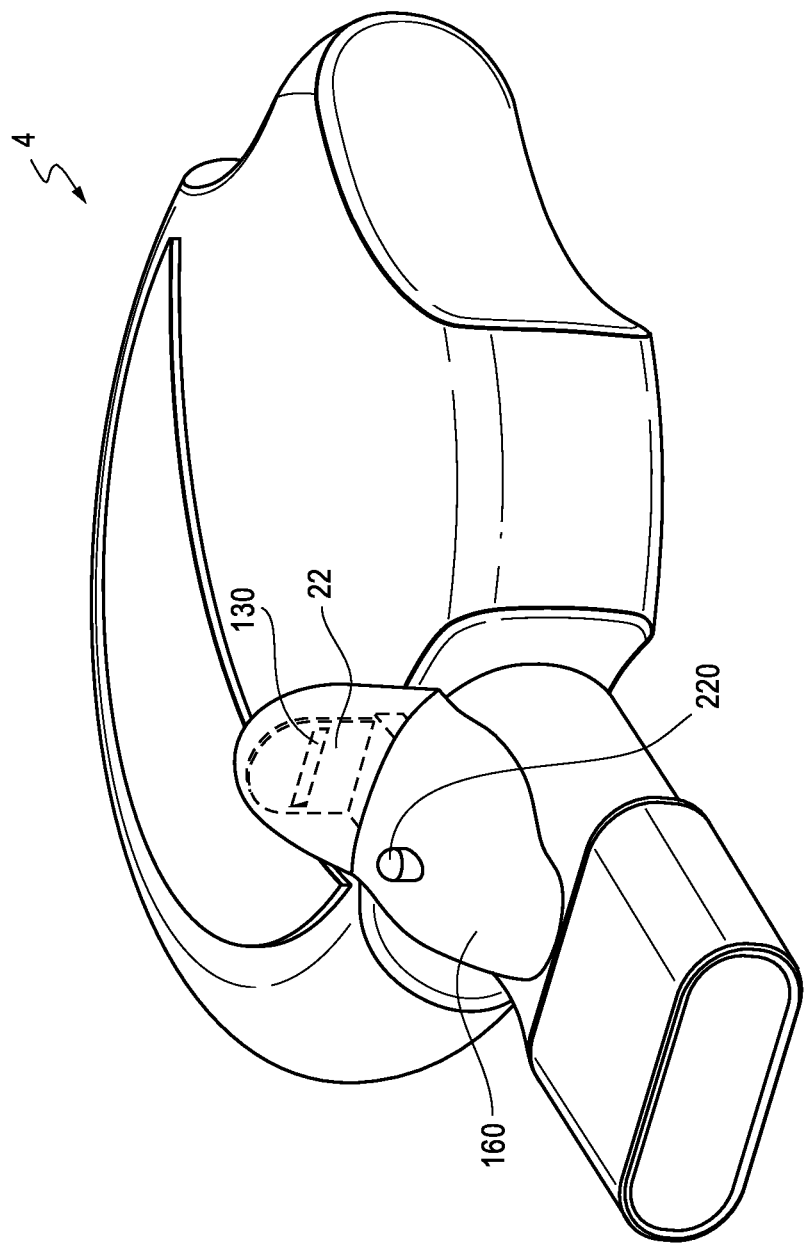
FIG. 10 is a perspective view of an embodiment of a dry powder inhaler having a flow indicator and an electronic indicator.
Figure 11:
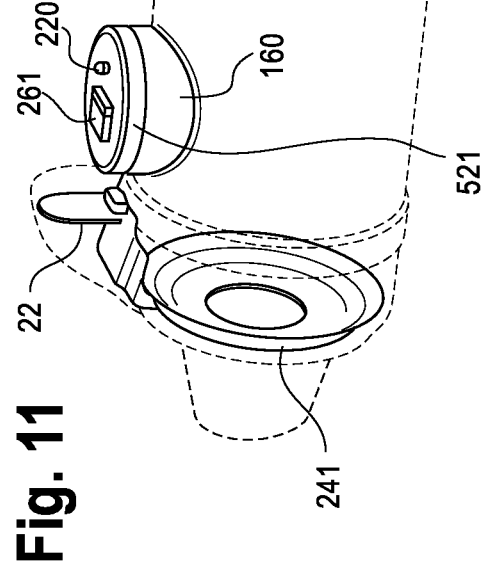
FIG. 11 is a partial, perspective view of a valved holding chamber with a flow indicator and an electronic indicator.
Figure 12B:
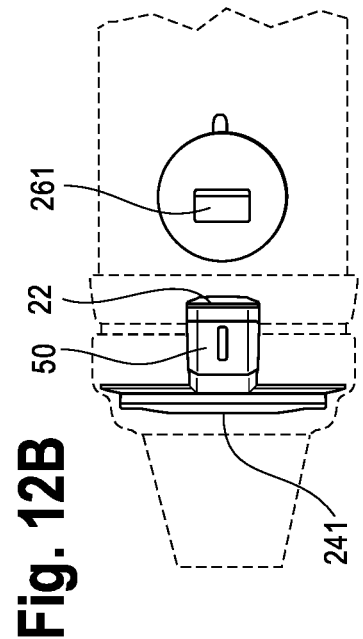
FIGS. 12A and B are side and top views of the valved holding chamber shown in FIG. 11.
Figure 12A:
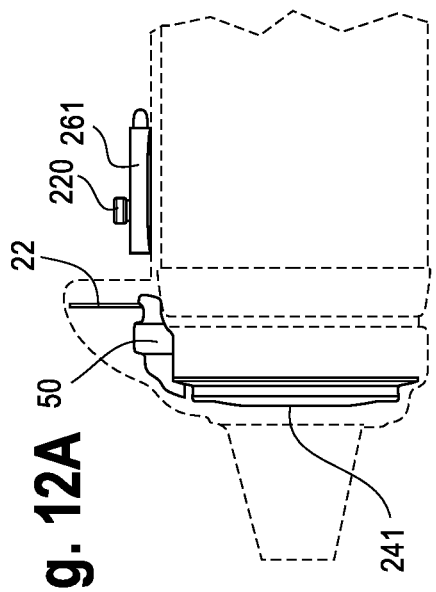
Figure 19:
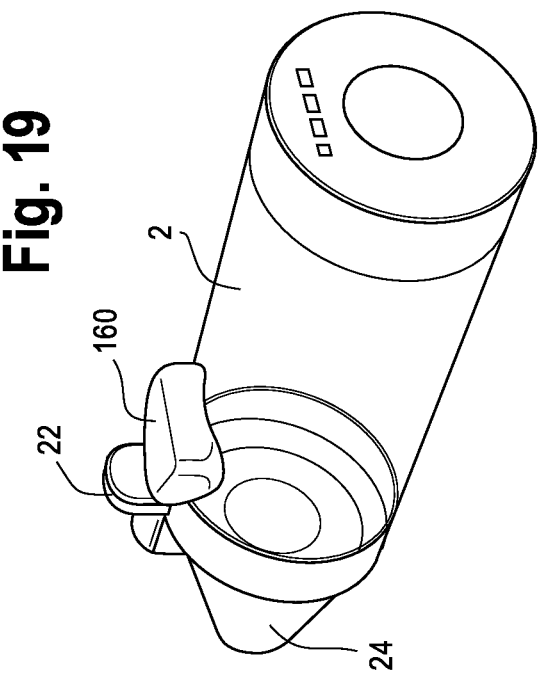
FIGS. 18 and 19 are front and rear perspective views of the valved holding chamber shown in FIG. 1.
Figure 18:
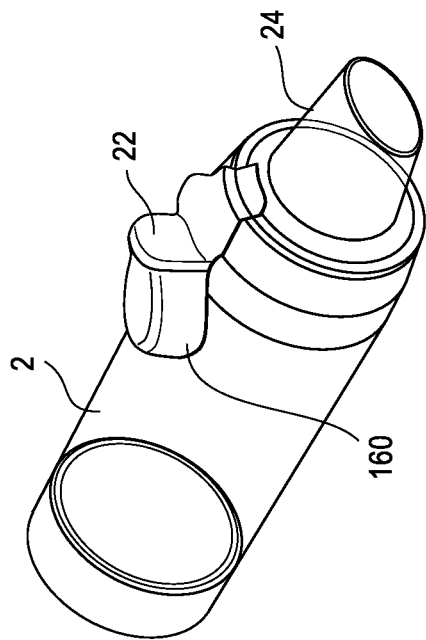

Referring to FIGS. 26, 27 and 42-43C, a mouthpiece 70, incorporated for example into a dry powder inhaler (FIG. 10), a nebulizer (FIG. 8), or a oscillating positive expiratory pressure device (FIG. 9), includes an exhalation valve 72 secured over an opening 74 in the mouthpiece, which defines a valve seat 76. The valve is configured with two flaps 78, such as a butterfly valve in one embodiment, with a central post or protuberance 82 extending through an opening 80 in the valve and securing it to the exterior of the mouthpiece. A shield (not shown) may be disposed over the valve to protect it from tampering.

Referring to FIGS. 28, 29, 33-35 and 44-45C, a nebulizer 90 includes a chamber 92, a diaphragm 96 and a dial 98 disposed on top of an actuator 94. The actuator 94 and dial 98 move axially along axis 107 during inhalation. A bottom 104 of the dial 98 engages an inner periphery of the diaphragm 96, and a bottom 102 of the actuator has a surface that engages a nozzle cover 100, as the actuator is moved axially downwardly during inhalation.

Referring to FIGS. 30A-32 and 46-48C, another embodiment of a valved holding chamber 110, which may be used for example and without limitation in a ventilator circuit, is shown. The valved holding chamber has a connector component 112, which defines a ventilator port. The connector has first and second passageways 114, 116 separated by a wall 118. An integrally formed inhalation/exhalation valve 120 has a pair of flaps 122, 124 extending from opposite directions from a base portion 126. The connector has a valve seat 128 for the inhalation valve 122, while the chamber has a valve seat 130 for the exhalation valve 124. Various aspects of the valved holding chamber and connector are disclosed in U.S. Pat. No. 8,875,706, the entire disclosure of which is hereby incorporated herein by reference.

It should be understood that various components of the above-described medicament delivery devices are flow indicators, and in particular mechanical flow indicators, which move dynamically in response to a flow. The various components, regardless of whether they are visible, provide indicia of a flow, whether inhalation or exhalation. The various components may or may not be visible to the user and/or caregiver. The movement of the flow indicators provides input to an electronic flow indicator that sufficient inhalation has occurred. For example, the number of movements of the flow indicator 22, whether upon inhalation or exhalation (or both), during a breathing cycle (defined as the number of breaths (N) taken while the medicament is being administered), or the cumulative duration (T) of the change of position of the flow indicator during the breathing cycle, provides input to the circuitry that is correlated with sufficient inhalation. Specifically, a predetermined number or duration (whether singular or cumulative) of contacts, or sufficient proximity to contact, between the flow indicator 22 and a seat, or contact point, provides input to and actuates the electronic indicator, for example by displaying a green light or other indicia. If the number of movements of the flow indicator, or the duration (singular or cumulative) thereof, is not achieved, or if sufficient contact(s) or proximity of contact(s) is not achieved, then the electronic circuit will not activate the electronic indicator, or alternatively, the electronic indicator may be activated to show inadequate medicament administration, for example by displaying a yellow or red light, an auditory signal, vibration (e.g., tactile) or other indicia.

For example, in one embodiment, as shown in FIGS. 1-6, 11-21 and 51-53, the visual flow indicator 22 defines a mechanical flow indicator having a conductive strip 130, or including other electrically conductive properties, which act as a (normally open) switch closing a circuit when it seals against a seat 132. The activation of the circuit by the closing of the switch thereby activates the electronic feedback utilizing low power circuitry enclosed within a portion of the user interface, such as a mouthpiece or mask adapter. The conductive properties may be specific to a small region of the flow indicator, e.g., a thin strip or other geometry, or the entire face of the flow indicator may be conductive. Alternatively, the system uses capacitive sensing to determine when the flow indicator has reached a second position corresponding to a predetermined flow. Feedback from the electronic indicator 220 indicates that a sufficient inhalation flow rate is achieved and/or that proper treatment has been completed based on a number of breaths and/or the volume calculated based on the minimum flow required to seal the mechanical flow indicator and/or the length to time in which the seal (switch) is maintained. The minimum flow required to seal the mechanical flow indicator may be between 3-5 L/min.

Figure 54:
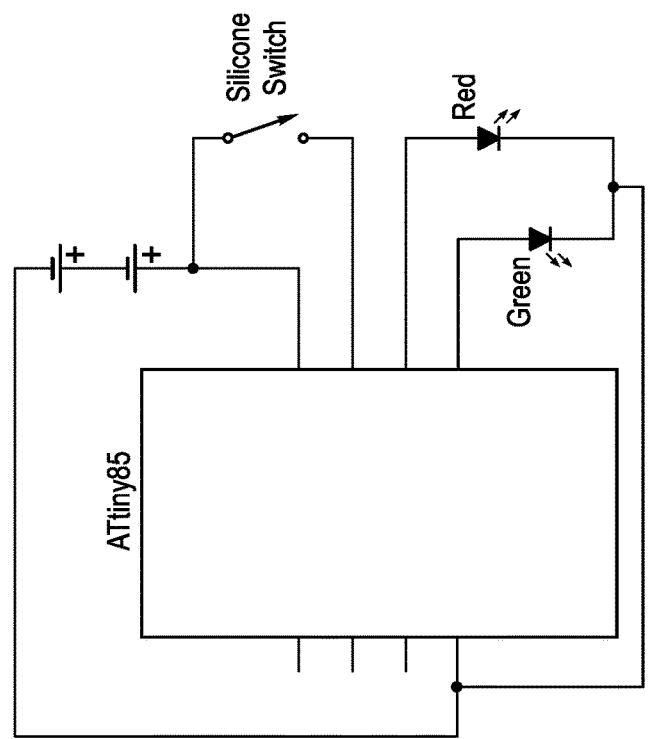
FIG. 54 is a schematic view of a microprocessor for an electronic indicator.

In other embodiments, the switch may be a normally closed switch, which activates the circuit when the switch is opened, for example when an inhalation or exhalation valve (flow indicator) is operated. Again, the number of movements of the flow indicator (e.g., inhalation or exhalation valve or actuator), or duration of the opening of the switch, may provide input to the circuit (FIG. 54) that sufficient medication delivery has been achieved, with the circuit then activating the electronic indicator. For example, and referring to the embodiments shown in FIGS. 22, 23, 38A-C, 39, 46-48C, 62 and 63 the mechanical flow indicator is defined by the inhalation valve 241, 122, 1060 which may function as the input or switch for the electronic feedback. Again, the inhalation valve may be configured with a region 150, 152 or material having conductive properties, for example around the inner or outer periphery 33 of the annular valve, or along a free end 154 of the inhalation flap 122, that mate with a mating surface, e.g., valve seat 42, 128, forming a part of an electronic circuit, for example in the baffle, also having a conductive material or region. In this embodiment, when the valve 241, 122 is in the closed position, flow is not sufficient and no electronic feedback is present. Once the valve (normally closed switch) moves to an open position, for example during inhalation, and is no longer in contact with a baffle, or valve seat, on which it is contact when closed, electronic feedback is activated. In the latter case, movement detection may be performed by a pressure sensor, a capacitive sensor, an inductive sensor, or other proximity sensor or switch. Upon reaching a predetermined second position, the electrically conductive properties of the indicator act as a switch, whether open or closed, to activate the electronic feedback utilizing low power circuitry enclosed with a housing 160, located on the chamber housing, mouthpiece, mask adapter or other component. The switch on the sealing surface 42, 128 where the flow indicator mates upon its second position may be configured as two small conductive point contacts or conductive pads, emerging from an encapsulated, potted, conformal coated or sealed printed circuit board (PCB) or microcontroller 261.

If the switch is created using capacitive sensing, the sensor within the encapsulation is a small pad with a sensing area no larger than 25 mm$^2$ and a ground pad matching the size of the PCB at a minimum to increase sensitivity of the sensor. The ground pad may be incorporated within the encapsulation or may be formed by a conductive path from the conductive region of the indicator along the body of the chamber. The human body may come in contact with the conductive path while holding the chamber and act as a ground.

Figure 62:
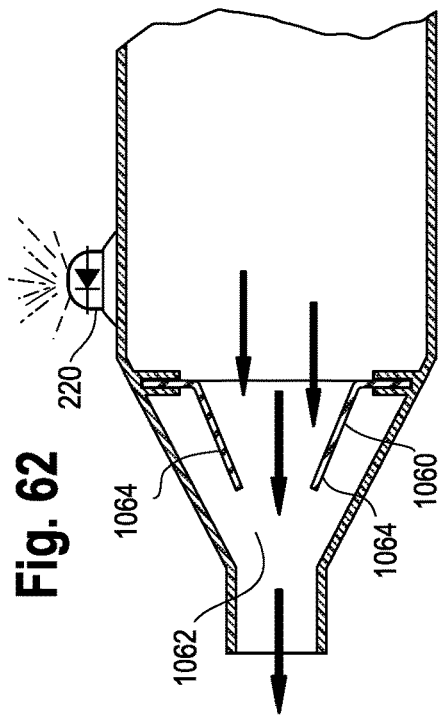
FIG. 62 is a cross-sectional view of one embodiment of a valved holding chamber.
Figure 63:
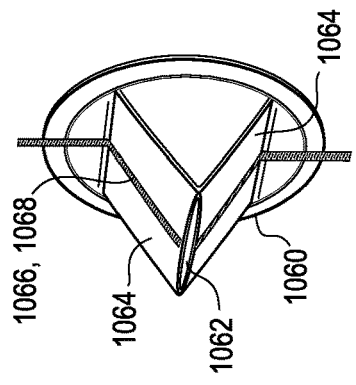
FIG. 63 is a perspective view of the inhalation valve used in the valved holding chamber of FIG. 62.

As shown in FIGS. 62 and 64, the mechanical flow indicator is configured as a duckbill valve 1060, which has a pair of flaps 1064 that open to form a central opening 1062 in response to a flow through the valve. The valve provides one-way flow control. The valve flaps 1064 may have conductive strips 1066 that are in contact with the valve is in a normally closed position, such that an opening of the valve cause the circuit to identify a flow and send a signal to an electronic indicator 220 and/or record an opening in a database. The valve flaps 1064 may alternatively be provided with a flexible resistor 1068, which deflects with the valve flaps, in a circuit that signals the electronic indicator 220 to provide indicia that flow has occurred, for example by illuminating. The sensor may alternatively be configured as a capacitive sensor.

The electronic components in the various embodiments may be integrated in the assembly of the device, or embodied in a modular component or housing 160 that can be fit to any valved holding chamber (or other respiratory device). In either scenario, the electronic components are encapsulated, potted, conformal coated or sealed in an area preferably between 25×25×5 mm (L×W×H) and 45×45×20 mm (L×W×H). It should be understood that the electronic indicator and flow indicator may be incorporated into a removable patient interface, e.g., mask, mouthpiece, adapter, etc., that may be used by the same patient/user with more than one respiratory care system. It should be understood that in the various embodiments, the circuitry is not visible to the user or caregiver.

Figure 50:
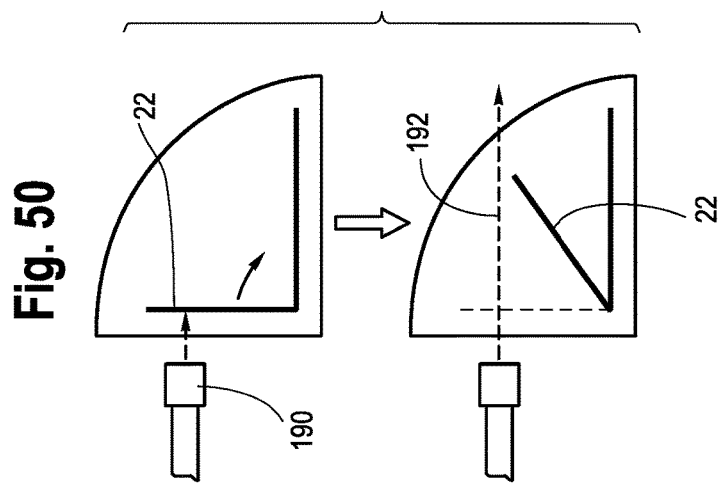
FIG. 50 is a schematic side view of an optic sensor interfacing with a mechanical flow indicator.
Figure 52:
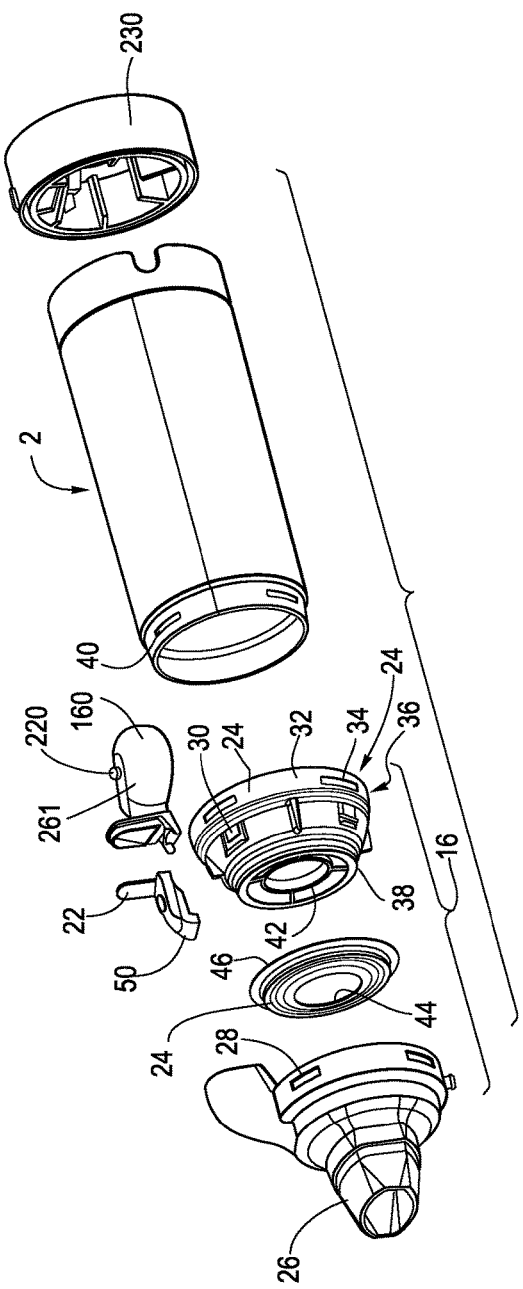
FIG. 52 is an exploded perspective view of one embodiment of a valved holding chamber assembly.
Figure 53:
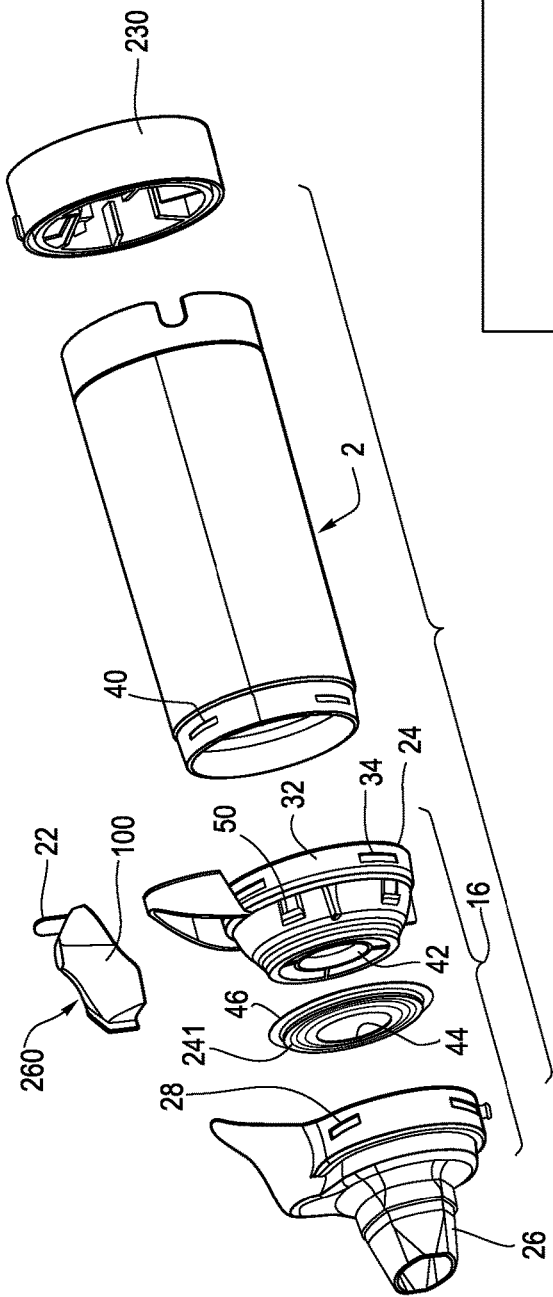
FIG. 53 is an exploded perspective view of another embodiment of a valved holding chamber assembly.

Other embodiments of the mechanical flow indicator include the exhalation valve 54, 72, 124 on the mask, mouthpiece or connector, which act as the switch (normally open or closed) described above. In each of these embodiments, the valve (or other moving member) has conductive properties in a region 180 (outer periphery of valve 54), 182 (periphery of valve 72), 184 (free edge of flap 124) in contact with a sealing surface 181, 76, whether in a normally open or closed configuration, also having a conductive material or region. While contact is maintained, the switch is on or off (dependent on what feedback is desired) and the switch changes state when flow is enabled to overcome the valve (or other moving member). Alternatively, a proximity sensor or switch may be incorporated into a chamber that accepts an MDI canister to provide indication that the canister is sufficiently inserted in the device. As shown in FIG. 50, an optic sensor 190 may be provided to signal 192 when the flow indicator 22 has moved to a second position, with sensor 190 providing input to the circuit. Referring to FIGS. 31, 32 and 46-48C, either of the multipurpose inhalation/exhalation valves 122, 124 on the chamber may be configured with a conductive material or region 152, 184 that closes a switch during inhalation and/or exhalation. The chamber may be utilized in combination with mechanical ventilation, a manual resuscitation bag or a standard aerosol resuscitation mask.

Alternatively, as shown in FIGS. 28, 29 and 33-35, the bottom 104 of the dial and an inner periphery 106 of the diaphragm on a nebulizer may be configured with a conductive material or region, which complete a switch when coming into contact, for example during inhalation as the actuator moves axially downwardly. Alternatively, as shown in FIGS. 44-45C, a bottom surface of the actuator has a conductive material or region that comes into contact with a conductive material or region on the muzzle cover 100 as the actuator moves axially, thereby closing or opening a switch as described above.

Figure 49:
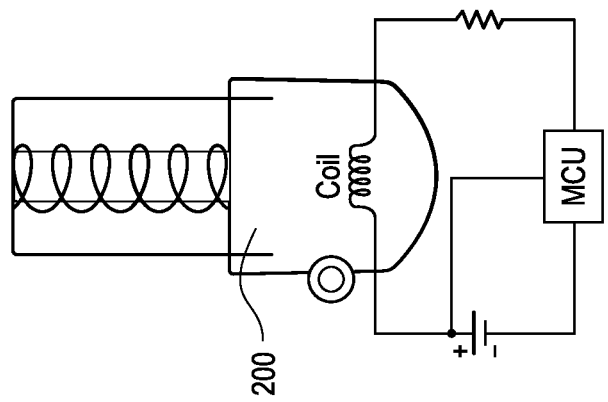
FIG. 49 is a schematic diagram of a manometer.
Figure 48B:
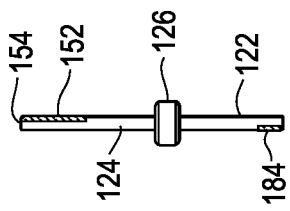
Figure 47:
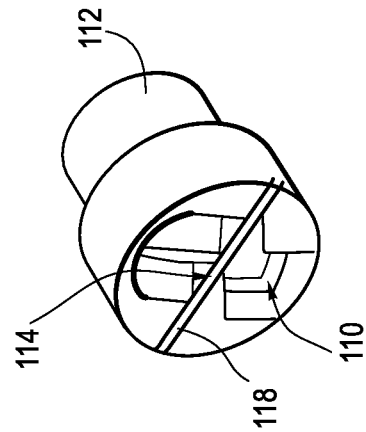
FIG. 47 is a perspective view of a connector for the holding chamber of FIG. 46.
Figure 46:
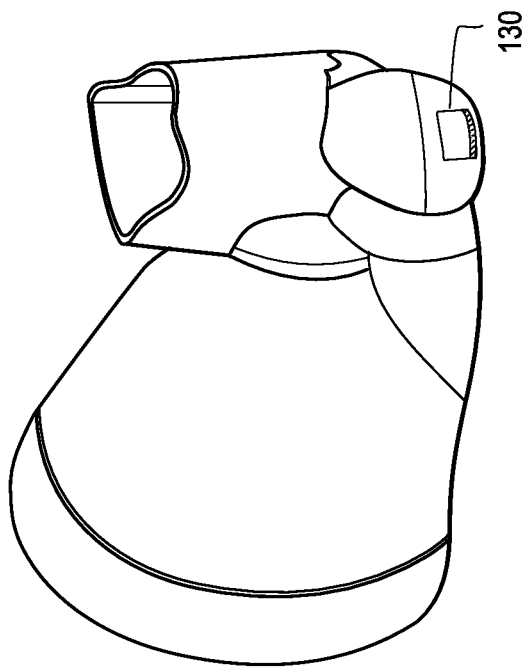
FIG. 46 is a perspective view of a holding chamber.
Figure 48A:
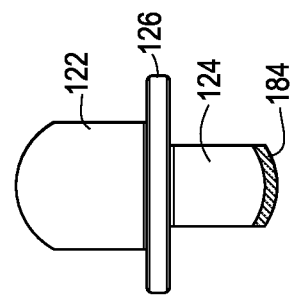

In other embodiments, shown in FIG. 49, a piston 200 on a manometer may be configured with a magnetic or conductive material or region, with a variable output relative to pressure provides an input to an electronic indicator. The various steps performed by the system are shown in the block/flow diagram of FIG. 7. The sensor or switch input, which may also be related to a mechanical feedback, relays information to a microcontroller unit 261. The microcontroller 261, also shown in FIGS. 3, 12A and B, 13 20 and 22, controls the electronic feedback output, and transmits a signal to the electronic indicator (e.g., LED) 220, and may provide output as disclosed herein. A light pipe may diffuse the light from the LED. A battery 521 provides power to the circuit.

The entirety of the system may be washed by the user without special attention to the electronics, which may also be configured to withstand the heat of a dishwasher. Alternatively, the electronics may be removed prior to washing or exposure to heat. In one embodiment, the battery chemistry is a lithium coin cell, specifically poly-carbon monofluoride lithium that is specifically designed to operate at temperatures up to 125C, has an annual deterioration rate as low as 0.5% and has a relatively flat discharge voltage curve. Incorporating sufficient thermal insulation properties in the encapsulation material may allow for the entirety of the device to withstand autoclaving processes.

Figure 36:
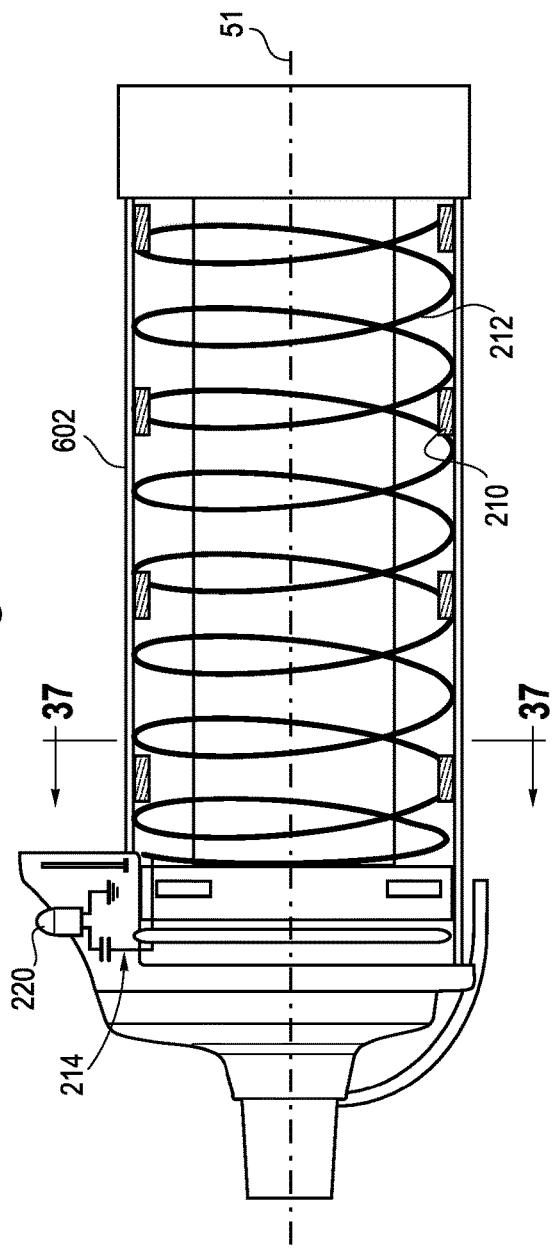
FIG. 36 is a side view of a holding chamber assembly.
Figure 37:
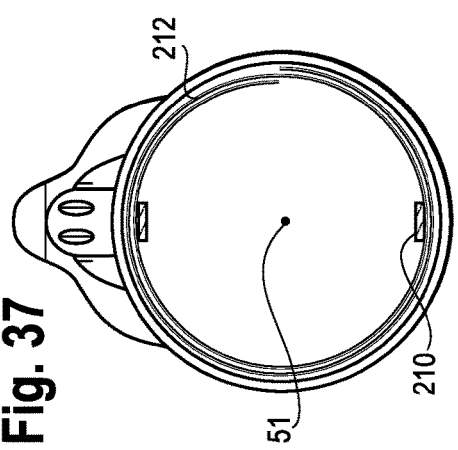
FIG. 37 is a cross-sectional view of the holding chamber assembly shown in FIG. 36 taken along line 37-37.
Figure 38C:
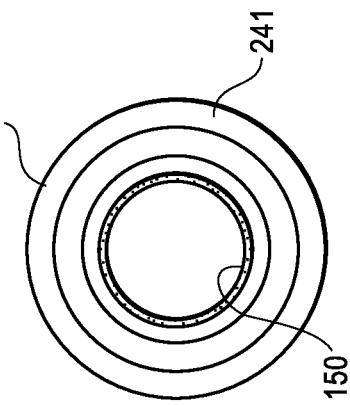
FIG. 38 is a back view of an inhalation valve for a valved holding chamber.
Figure 38B:
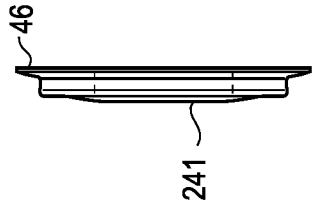
Figure 38A:
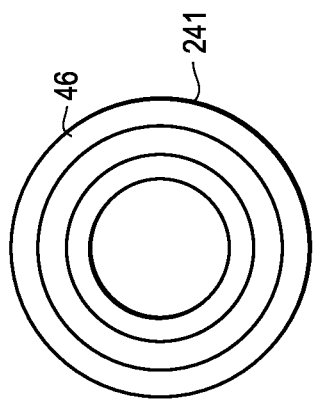
Figure 39:
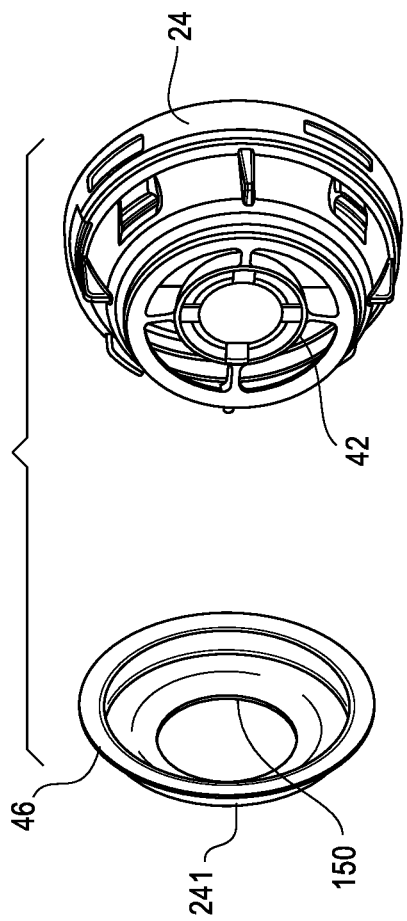
FIG. 39 is a perspective view of a retainer incorporated into a valved holding chamber.
Figure 41B:
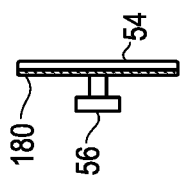
FIGS. 41A-C are front, side and rear views of valve incorporated into the mask shown in FIG. 40.
Figure 41A:
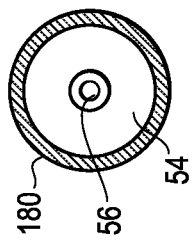
Figure 41C:
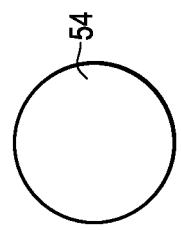
Figure 40:
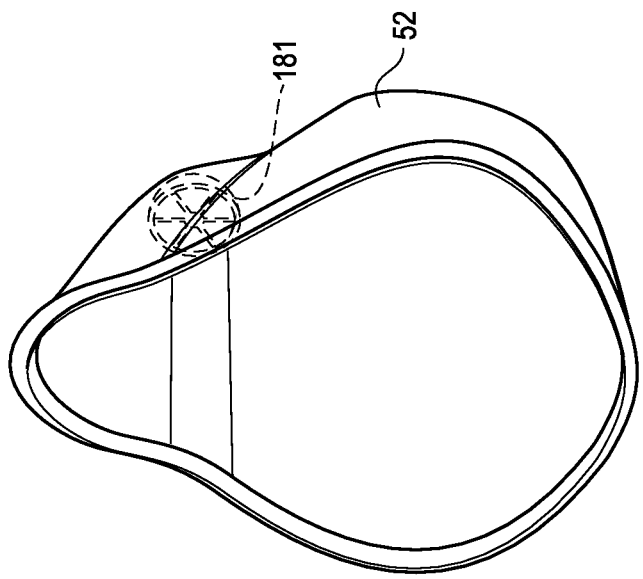
FIG. 40 is a perspective view of a mask.
Figure 48C:
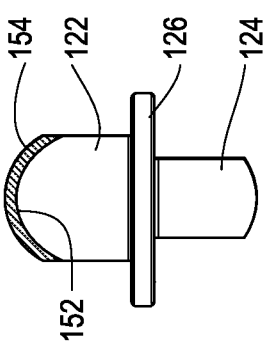
FIGS. 48A-C are front, side and rear views of a combined inhalation/exhalation valve incorporated into the holding chamber of FIG. 46.

In an alternative embodiment, shown in FIGS. 36-37, linear induction may be utilized to generate power for the circuit and thereby eliminate the need for a battery. The linear electrical generator is composed of one or more neodymium magnet(s) 210 that move reciprocally back and forth along a longitudinal axis 51 (or parallel thereto) or direction within a center space defined by a copper coil 212 wrapped around the axis 51 when a chamber 602 is shaken. This shaking motion is necessary prior to actuating an MDI 13, 15 and does not imply an additional step in the drug delivery process. The shaking induces a current in the coil 212, which is stored in a supercapacitor 214 to power the circuitry connected to an electronic indicator 220.

When taking the device out of the package the first time, an internal timer on the device will activate. For example, a light sensor (or other sensor) will activate an internal clock to begin tracking elapsed time. Alternatively, the timer may be activated upon the first use. The device will function as described herein for the duration of a predetermined recommended life of the device as determined by the timer, at which point the electronic indicator will either stop functioning or produce a warning signal different from the previously seen signal that indicates prior inhalation and/or treatment completion. This warning signal (e.g., red LED) will indicate to the user that it is time to dispose of the chamber. Nonetheless, the mechanical flow indicator will continue to function after the expiration of the predetermined recommended life, e.g., 1 year, so as to not diminish the safe use of the device.

The user interface, including for example the mouthpiece or mask adapter, holding chamber and retainer may be made of transparent anti-static material (ABS). A back-piece 230, which interfaces with a MDI 13, 15, may be made of an ultra-soft thermoplastic elastomer. The inhalation valve may be made of silicone. The mechanical flow indicator may be made of silicone with magnetic or conductive properties, including a conductive region made of a conductive silicone, metal foil or a conductive coating/ink. The conductive materials may be silver oxide, carbon black, aluminum, or other known conductive materials. The electronics, such as the microcontroller 261, may be potted conformal coated, sealed, or encapsulated in silicone, epoxy, urethane, hot melt or other materials resistant to high temperatures.

In one embodiment, the electronic indicator 220 is a visual indicator (e.g., LED or LCD display), which provides the electronic feedback. Other electronic indicators may be used, for example an audible signal or feedback, such as a buzzer, a sequence of LED's or other visual cues showing a percentage of treatment completion (e.g., LED bar graph), a segmented numerical display of the treatment percentage completed, an LED or OLED screen showing the progress or numerical representation of the flow or volume remaining, or possible connection to and communication with a smart phone application via bluetooth low energy (BLE) to show data from inhalation or to incorporate flow data into a game.

In operation, as illustrated in FIG. 67, when the MDI or other drug delivery device is actuated, a medicament will fill the chamber, for example when an inhalation valve is closed. The mechanical flow indicator, whether separately configured or defined by the inhalation valve, or actuator, is in a neutral position since no inhalation is taking place. Accordingly, the electronic indicator, e.g. LED, is off as no feedback is being provided. As the user begins to inhale, the inhalation valve will open, creating a negative pressure and causing the mechanical flow indicator to move forward from a first position to a second position until the flow indicator creates a seal with a seat at a predetermined, sufficient inhalation flow. When the flow indicator creates a seal with the seat, or is sufficiently proximate thereto, a circuit is closed and the electronic feedback is activated, for example by an LED, which provides feedback to indicate proper inhalation. For example, a green LED will provide positive feedback. The LED will stay illuminated while the seal is maintained, and turns off when the seal is broken, e.g., at the end of inhalation or upon improper inhalation. The circuit and electronic indicator may also be configured to be activated when a predetermined number of movements of the flow indicator, or a cumulative duration of such movements, has been achieved. Alternatively, or in addition to indicating proper individual inhalations, the LED may illuminate and stay on for an extended period of time when treatment is complete to relay that the user has completed a successful treatment, for example requiring multiple breathing cycles.

The same process occurs with the exhalation valves or nebulizer actuators configured as the flow indicator, but with the opening of the exhalation valve or actuator closing or opening a circuit so as to provide feedback via the electronic indicator.

At the end of predetermined life for the chamber or other components (e.g., 1 year), as tracked for example by the internal timer or clock, the LED will be deactivated, or the LED will provide a warning signal (e.g., turn red), indicating that the device should be replaced. In the former embodiment, with the lack of positive LED feedback during inhalation, the user will be made aware that the device should be replaced.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A user interface for a respiratory care system comprising:
    an inlet adapted to be connected to a respiratory device;
    an outlet adapted to interface with a user, wherein an inhalation flow path is defined between the inlet and the outlet;
    a flow indicator positioned outside the inhalation flow path, wherein the flow indicator is moveable from a first, at rest, closed position to a second, actuated, open position at least in response to inhalation by a user through the outlet;
    an optic sensor directed at and configured to sense when the flow indicator has moved from the first position to the second position, wherein the optic sensor is configured to provide an input signal when the flow indicator has moved from the first position to the second position;
    a controller configured to receive the input signal from the optic sensor and to transmit a feedback signal; and
    a feedback device operable to provide feedback about the inhalation flow in response to the feedback signal transmitted from the controller.

2. The user interface of claim 1 wherein the flow indicator is visible to the user.

3. The user interface of claim 1 wherein the outlet comprises at least one of a mask and/or mouthpiece.

4. The user interface of claim 1 wherein the feedback device comprises an electronic indicator.

5. The user interface of claim 4 wherein the electronic indicator comprises at least one of a visual indicator, audible indicator and/or a vibratory indicator.

6. A respiratory care system comprising:
    a respiratory device; and
    a user interface comprising:
        an inlet connected to a respiratory device;
        an outlet adapted to interface with a user, wherein an inhalation flow path is defined between the inlet and the outlet;
        a flow indicator positioned outside the inhalation flow path, wherein the flow indicator is moveable from a first, at rest, closed position to a second, actuated, open position at least in response to inhalation by a user through the outlet;
        an optic sensor directed at and configured to sense when the flow indicator has moved from the first position to the second position, wherein the optic sensor is configured to provide an input signal when the flow indicator has moved from the first position to the second position;
        a controller configured to receive the input signal from the optic sensor and to transmit a feedback signal; and
        a feedback device operable to provide feedback about the inhalation flow in response to the feedback signal transmitted from the controller.

7. The respiratory care system of claim 6 wherein the flow indicator is visible to the user.

8. The user interface of claim 6 wherein the outlet comprises at least one of a mask and/or mouthpiece.

9. The user interface of claim 6 wherein the feedback device comprises an electronic indicator.

10. The user interface of claim 9 wherein the electronic indicator comprises at least one of a visual indicator, audible indicator and/or a vibratory indicator.

11. The user interface of claim 6 wherein the respiratory device comprises one of a valved holding chamber, an oscillating positive expiratory pressure device, a nebulizer or a dry powder inhaler.

12. A method of treating a respiratory system of a user comprising:
    inhaling and/or exhaling through an outlet of a user interface;
    creating an inhalation flow along an inhalation flow path through the user interface between an inlet and the outlet when inhaling through the outlet, wherein a respiratory device is connected to the inlet;
    moving a flow indicator positioned outside the inhalation flow path from a first, at rest, closed position to a second, actuated, open position at least in response to the inhaling;
    sensing when the flow indicator is moved from the first position to the second position with an optic sensor;
    providing an input signal with the optic sensor when the flow indicator has moved from the first position to the second position;
    receiving the input signal with a controller;
    transmitting a feedback signal with the controller; and
    providing feedback to the user about the inhalation flow with a feedback device in response to the feedback signal transmitted from the controller.

13. The method of claim 12 wherein the flow indicator is visible to the user.

14. The method of claim 12 wherein the outlet comprises at least one of a mask and/or mouthpiece.

15. The method of claim 12 wherein the feedback device comprises an electronic indicator.

16. The method of claim 15 wherein the electronic indicator comprises at least one of a visual indicator, audible indicator and/or a vibratory indicator.

17. The user interface method of claim 12 wherein the respiratory device comprises one of a valved holding chamber, an oscillating positive expiratory pressure device, a nebulizer or a dry powder inhaler.

* * * * *